United States Patent
Espino et al.

(10) Patent No.: US 10,376,561 B1
(45) Date of Patent: Aug. 13, 2019

(54) FASCIOLA HEPATICA FATTY ACID BINDING PROTEIN A NOVEL ANTI-INFLAMMATORY MOLECULE

(71) Applicants: Ana M. Espino, San Juan, PR (US); Ivelisse Martin, San Juan, PR (US)

(72) Inventors: Ana M. Espino, San Juan, PR (US); Ivelisse Martin, San Juan, PR (US)

(73) Assignee: University of Puerto Rico, San Juan, PR (US)

( * ) Notice: Subject to any disclaimer, the term of this patent is extended or adjusted under 35 U.S.C. 154(b) by 0 days.

(21) Appl. No.: 15/156,284

(22) Filed: May 16, 2016

Related U.S. Application Data

(60) Provisional application No. 62/161,582, filed on May 14, 2015.

(51) Int. Cl.
*A61K 38/16* (2006.01)

(52) U.S. Cl.
CPC .................................... *A61K 38/16* (2013.01)

(58) Field of Classification Search
None
See application file for complete search history.

(56) References Cited

PUBLICATIONS

Abán et al., "A fatty acid binding protein from Fasciola hepatica induced protection in C57/BL mice from challenge infection with Schistosoma bovis", Veterinary Parasitology, 1999, 107-121.*
What is schistosomiasis?, www.yourgenome.org/facts/what-is-schistosomiasis, accessed Apr. 14, 2017, p. 1-13.*
Martin et al., "Fasciola hepatica Fatty Acid Binding Protein Inhibits TLR4 Activation and Suppresses the Inflammatory Cytokines Induced by Lipopolysaccharide In Vitro and In Vivo", The Journal of Immunology, Prepublished online Mar. 16, 2015 (Year: 2015).*

* cited by examiner

*Primary Examiner* — Lianko G Garyu
(74) *Attorney, Agent, or Firm* — Hoglund & Pamias, PSC; Roberto J. Rios

(57) ABSTRACT

Toll-like receptor 4 (TLR4), the innate immunity receptor for bacterial endotoxins, plays a pivotal role in the induction of inflammatory responses. There is a need to develop molecules that block either activation through TLR4 or the downstream signaling pathways to inhibit the storm of inflammation typically elicited by bacterial lipopolysaccharide (LPS), which is a major cause of the high mortality associated with bacterial sepsis. The present invention provides that a single intraperitoneal injection of 15 μg *Fasciola hepatica* fatty acid binding protein (Fh12) 1 hour before exposure to LPS suppressed significantly the expression of serum inflammatory cytokines in a model of septic shock using C57BL/6 mice. Whereas Fh12 alone did not induce cytokine expression, it significantly suppressed the expression of IL12, TNFα, IL6 and IL1β cytokines as well as iNOS2 in bmMΦs, and also impaired the phagocytic capacity of bmMΦs. One mechanism used by Fh12 to exert its anti-inflammatory effect is binding to the CD14 co-receptor. Moreover, it suppresses phosphorylation of ERK, p38 and JNK.

11 Claims, 21 Drawing Sheets
(3 of 21 Drawing Sheet(s) Filed in Color)

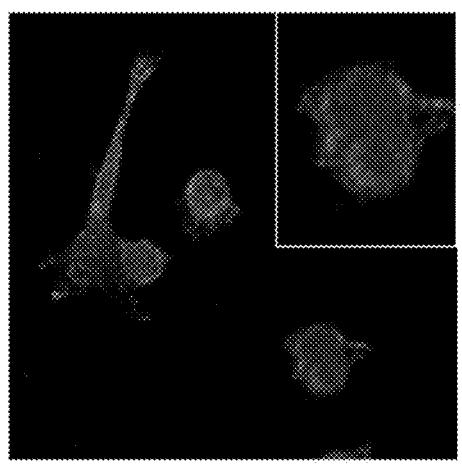
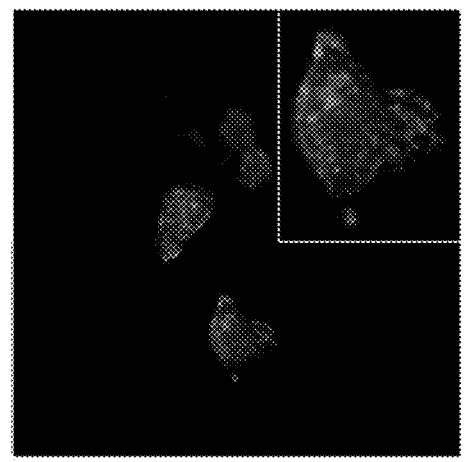
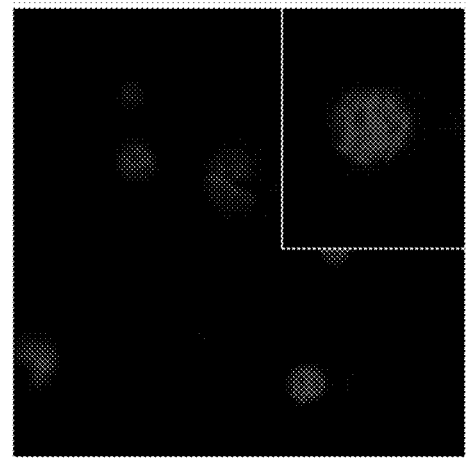
Figure 9A
Figure 9B
Figure 9C

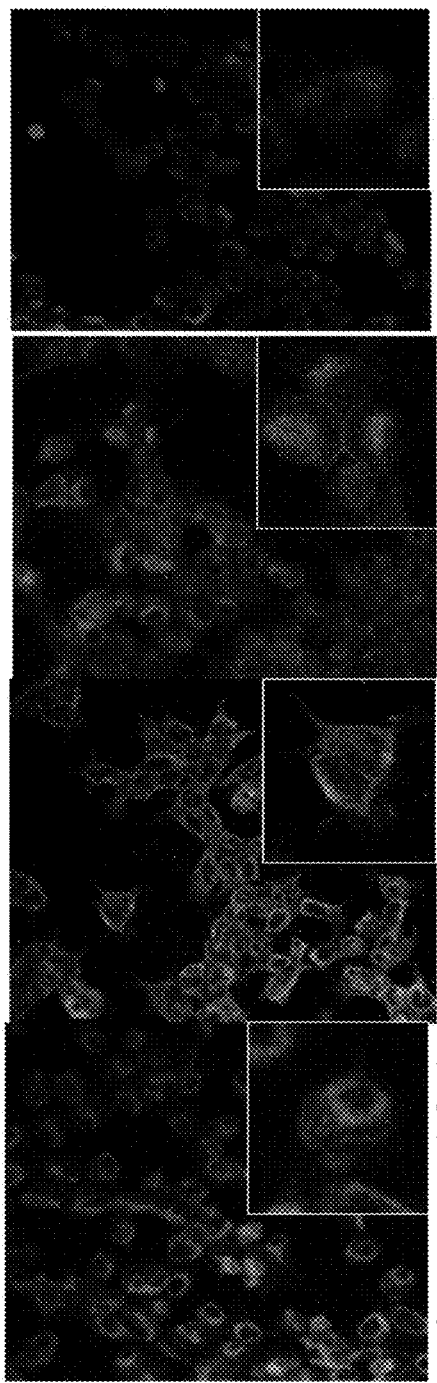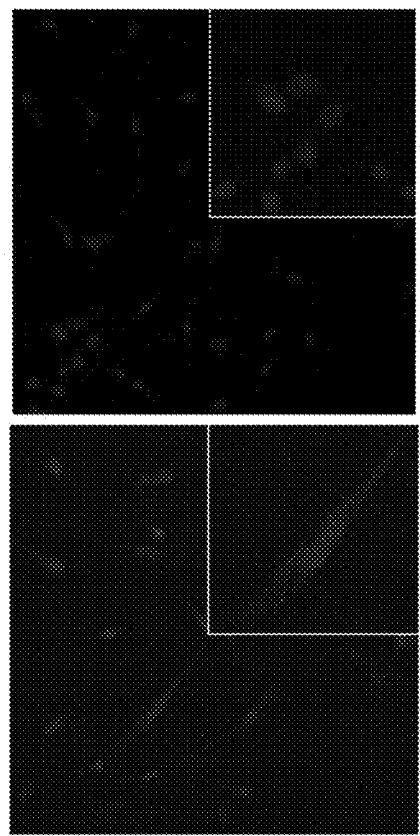
Figure 12A Figure 12B Figure 12C Figure 12D Figure 12E Figure 12F

FASCIOLA HEPATICA FATTY ACID BINDING PROTEIN A NOVEL ANTI-INFLAMMATORY MOLECULE

GOVERNMENT INTEREST

The claimed invention was made with U.S. Government support under grant number NIH 1SC1AI096108-01A2 awarded by The National Institutes of Health (NIH). The government has certain rights in this invention.

BACKGROUND OF THE INVENTION

Helminths, known as 'masters of immunomodulation', use several immunomodulatory strategies to evade and/or modify immune responses in order to survive into the mammalian host for long periods of time. The parasitic helminth *Fasciola hepatica* causes fascioliasis, an emerging important human disease that affects around 17 million persons worldwide. Fascioliasis also infects livestock, causing economic losses estimated at more than $3 billion annually. As with many other helminths, *F. hepatica* polarizes the immune system of the host to a dominant Th2/T-regulatory status with suppression of inflammatory responses. As a result, hosts infected with *F. hepatica* are rendered more susceptible to secondary bystander infections, such as with *Bordetella pertussis* and *Mycobacterium tuberculosis*, which require Th1 immunity for protection.

The potent immune suppression exerted by *F. hepatica* is mediated by the copious amounts of excretory-secretory products (ESPs) released by the parasite, particularly the cathepsin-L peptidases, which represent approximately 80% of ESPs. Studies have demonstrated that ESPs of *F. hepatica* can mimic the immunomodulatory effect that is observed during active infection, without the tissue pathology, and also suppress the development of the Th1 response. For example, administration of *F. hepatica* Cathepsin-L1 (CatL1) cysteine protease suppressed the onset of protective Th1 immune responses to bacterial infections in mice and prevented the development of a Th1 response in mice inoculated with *B. pertussis* vaccine. Glutathione S-transferase (GST), another major antigen comprising 4% of ESPs, inhibited the proliferation of rat spleen cells in response to ConA stimulation in vitro. Both CatL1 and GST were shown to partially activate dendritic cells (DCs) via toll-like receptor-4 (TLR4), a pattern recognition receptor (PRR), using different intracellular signaling pathways. Other *F. hepatica* polypeptides that also play a role in host immunomodulation are the tegument antigens. The tegument constitutes the parasite-host interface and is the place where much of the immune interplay between the fluke and host occur. *F. hepatica* tegument antigens have been shown to significantly suppress the serum levels of gamma interferon (IFNγ) and interleukin-12p'70 (IL12p70) and to suppress expression of the cell-surface markers CD80, CD86 and CD40 by targeting multiple TLRs of DCs. Moreover, *F. hepatica* tegument antigens have also been shown to impair DC function in a mouse model of septic shock by inhibiting their phagocytic capacity and ability to prime T cells.

Proteomic studies have demonstrated that both ESPs and tegument antigens consist of highly complex mixtures of polypeptides that include proteolytic enzymes, transporters, membrane-associated proteins, antioxidants and many other trematode-specific proteins. Members of the 12 kDa fatty acid binding protein (FABP) family have been identified in most of these studies. FABPs play an essential role in parasite nutrition and have been recently categorized as antioxidant molecules. These proteins can potentially prevent oxidative damage to trematode cellular components by binding fatty acids and ions involved in oxidative stress. Previous studies have shown that vaccines containing FABPs induce partial immune protection in experimentally infected mice and sheep. Moreover, *F. hepatica* FABPs also appear to be important molecules for inducing cross-immunity against *Schistosoma* species. Although numerous published papers have explored the vaccine potential of *F. hepatica* FABPs, no studies have investigated whether FABPs have anti-inflammatory effects or whether they may interact with cells of the host immune system.

In the present invention, we purified native forms of FABP (named Fh12) from adult fluke extract for the anti-inflammatory properties of the purified protein in vitro and in vivo. This invention is the first to present the anti-inflammatory properties of *F. hepatica* fatty acid binding protein, providing evidence of its mechanism of action.

SUMMARY OF THE INVENTION

The present invention either blocks activation through TLR4 or the downstream signaling pathways to inhibit the storm of inflammation typically elicited by bacterial lipopolysaccharide (LPS). A single intraperitoneal injection of *Fasciola hepatica* fatty acid binding protein (Fh12) prior to LPS exposure suppressed significantly the expression of serum inflammatory cytokines in a model of septic shock using C57BL/6 mice. Fh12 alone significantly suppressed the expression of IL12, TNFα, IL6 and IL1β cytokines as well as iNOS2 in bmMΦs, and also impaired the phagocytic capacity of bmMΦs. One mechanism used by Fh12 to exert its anti-inflammatory effect is binding to the CD14 co-receptor. Moreover, it suppresses phosphorylation of ERK, p38 and JNK. The potent anti-inflammatory properties of Fh12 demonstrated here indicates the potential of this molecule as a new class of drug against septic shock or other inflammatory diseases. According to an aspect of the invention, a method of reducing TLR4 mediated inflammation on a mammal is proposed.

According to another aspect of the invention, the mammal is administered an amount of *Fasciola hepatica* fatty acid binding protein (Fh12).

According to still another aspect of the invention, *Fasciola hepatica* fatty acid binding protein (Fh12) specifically binds to a CD14 co-receptor of a TLR4 protein effectively reducing TLR4 mediated inflammation on said mammal.

According to yet another aspect of the invention, TLR4 mediated inflammation is reduced by blocking interactions between TLR4 and bacterial Lipopolysaccharide (LPS) According to an aspect of the invention, TLR4 mediated inflammation is reduced by suppressing the expression of at least one inflammatory cytokine.

According to another aspect of the invention, TLR4 mediated inflammation is reduced by suppressing the expression of IFNγ, TNFα, IL-1β and IL-12.

According to one aspect of the invention, *Fasciola hepatica* fatty acid binding protein (Fh12) impairs the phagocytic capacity of bone marrow-derived macrophages (bmMΦs). According to still another aspect of the invention, *Fasciola hepatica* fatty acid binding protein (Fh12) suppresses the expression of inducible nitric oxide synthase (iNOS2) in bone marrow-derived macrophages (bmMΦs).

In accordance with another aspect of the invention, the administration of said *Fasciola hepatica* fatty acid binding protein (Fh12) prevents TLR4-induced septic shock on said mammal.

According to another aspect of the invention, *Fasciola hepatica* fatty acid binding protein (Fh12) is administered intraperitoneally.

According to still another aspect of the invention, *Fasciola hepatica* fatty acid binding protein (Fh12) is administered with an adjuvant.

According to yet another aspect of the invention, *Fasciola hepatica* fatty acid binding protein (Fh12) is administered prior or after the mammal being exposed to bacterial Lipopolysaccharide (LPS).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Further features and advantages of the invention will become apparent from the following detailed description taken in conjunction with the accompanying figures showing illustrative embodiments of the invention, in which:

FIG. 9A shows images representing cells treated with LPS and incubated with the pair of antibodies mouse anti-lipid A IgG and goat anti-CD14 IgG, according to the present invention.

FIG. 9B shows images representing cells treated with Fh12 incubated with the pair of antibodies anti-Fh12 IgG) and goat anti-CD14 IgG, according to the present invention.

FIG. 9C shows images representing control cells treated with PBS and incubated with the pair of antibodies anti-lipid A IgG or anti-Fh12 IgG and anti-CD14 IgG, according to the present invention.

FIGS. 12A-12F show images confirming that Fh12 binds to the CD14-coreceptor, according to the present invention.

DETAILED DESCRIPTION OF THE INVENTION

Materials and Methods

Animals

Figure 1:
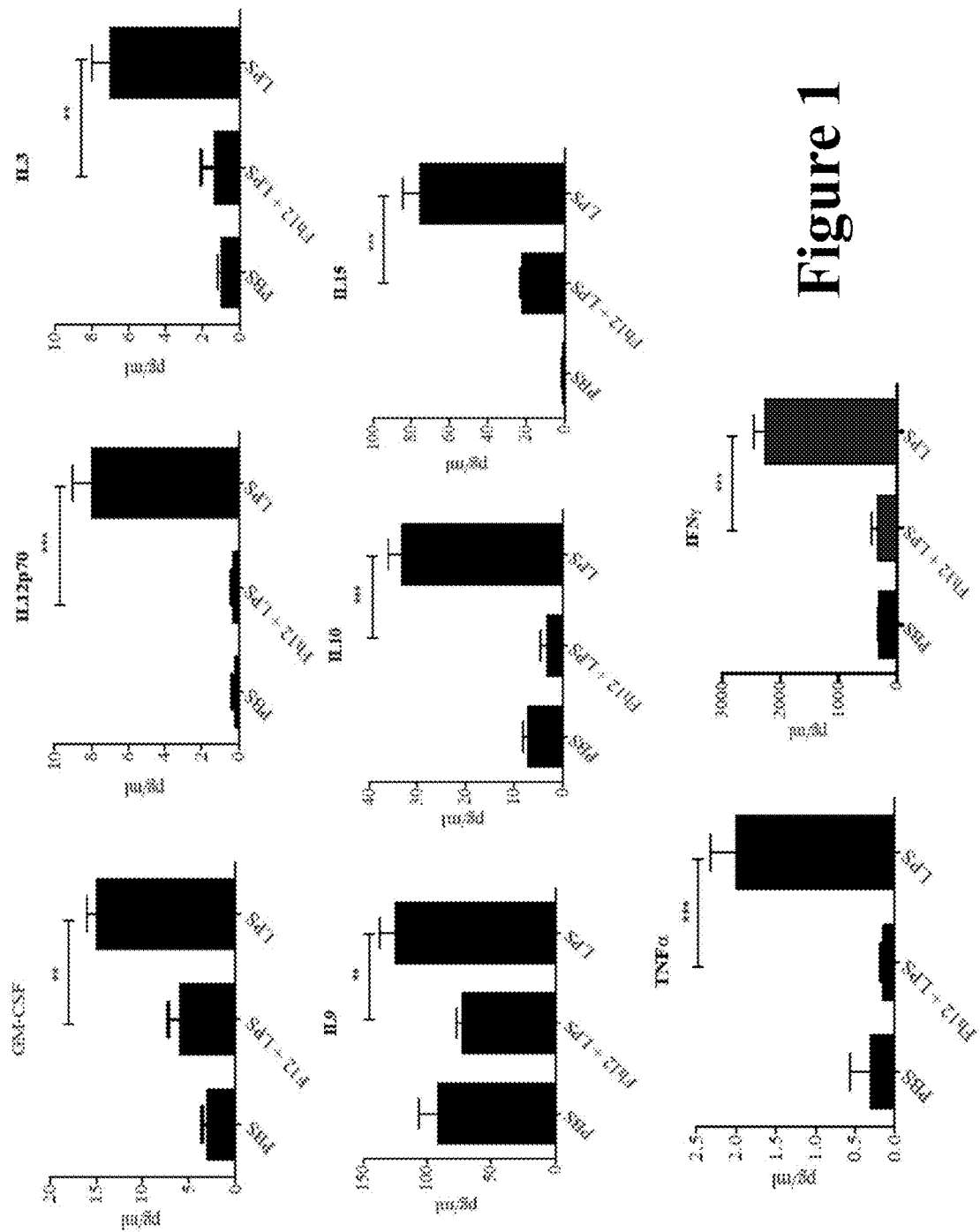
FIG. 1 shows plots of serum IFNγ, IL12p70, TNFα, GM-CSF, IL3, IL9, IL10, and IL15 cytokines levels, according to the present invention.

C57BL/6 female mice, 6 to 8 weeks old, were purchased from Charles River (Charles River Lab. Inc., Wilmington Mass., USA). B6.12954 CD14 knockout (CD14$^{-/-}$) female mice (on C57BL/6 background), 6 to 8 weeks old, were purchased from Jackson Laboratory (Bar Harbor, Me.). All mice were kept under conventional germ-free conditions in the animal care facility of the University of Puerto Rico School of Medicine and treated according to Institutional Animal Care and Use Committee Standards (IACUC protocol #7870215).

Preparation of Soluble Whole Worm Extract of Adult *F. hepatica* (FhWE)

*F. hepatica* adult worms were homogenized with a Teflon homogenizer in 0.1M phosphate buffered saline (PBS), pH 7.4, in the presence of a protease inhibitor cocktail and then centrifuged at 30,000×g for 30 min at 4° C. as previously described. The supernatant was used immediately or stored at −20° C. until use for the purification of FABPs.

Purification of 12 kDa Native Fatty Acid Binding Protein from *F. hepatica* (Fh12)

Native Fh12 was purified from FhWE using a previously optimized protocol that involves an initial ultracentrifugation step at 30,000×g, followed by gel filtration chromatography with Sephadex G-50 (XK 26/100 column) and two consecutive preparative isoelectric focusing (IEF). Each aliquot from the last IEF separation was subjected to 12.5% SDS-PAGE and the proteins were visualized by silver staining or coomassie blue staining. Fractions that exhibited a single polypeptide band of around 12 kDa were manually excised from the gel and their identity as FABP confirmed by MALDI and MS/MS as previously described. Fractions were pooled and termed Fh12.

Production of Anti-Fh12 Polyclonal Antibody

A New Zealand White rabbit was immunized by subcutaneous injection with 200 μg of purified Fh12 protein mixed with an equal amount of complete Freund's adjuvant. The rabbit was boosted twice with equal amounts of protein mixed with incomplete Freund's adjuvant at 2-week intervals. The rabbit IgG fraction was purified using protein-A affinity chromatography (GE Healthcare).

Endotoxin Removal

Endotoxins were removed from the Fh12 by using polymyxin B (PMB)-columns (31) according to the manufacturer's instructions. The presence of endotoxins was assessed prior to and after removing endotoxins using the Chromogenic Limulus Amebocyte Lysate (LAL) QCL-1000 Assay (Lonza, Walkersville, Md., USA) following the manufacturer's instructions. Endotoxin levels were quantified using a standard curve and reported as endotoxin units/ml (EU/ml). Protein concentration was adjusted to 1 mg/ml as determined by the bicinchoninic acid (BCA) method using a Pierce protein assay kit (Pierce, Cambridge, NJ). Purified endotoxin free Fh12 was stored in aliquots at −20° C. until use.

Septic Shock

Groups of 5 animals each were injected intraperitoneally (i.p.) with Fh12 (15 μg for each mouse), 1 h before i.p. injection with LPS (*E. coli* 0111:B4, 1 μg per each mouse). Control mice received PBS, Fh12 or LPS only (i.p.). Mice were sacrificed by cervical dislocation 12 h later, and blood samples were collected from orbital vein or by cardiac puncture. Serum concentration of IFNγ, IL12p70, TNFα, GM-CSF, IL3, IL9, IL10, IL15, and IL10 and were measured by cytokine microarrays (RayBiotech, GA, USA).

Isolation and Treatment of Bone Marrow-Derived Macrophages (bmMΦs)

Cells were collected from femoral shafts of mice by flushing with 3 ml of cold sterile PBS. The cell suspension was passed through a sieve to remove large clumps, washed 3 times with sterile complete RPMI medium (supplemented with 20 mM L-glutamine, 1 ml penicillin and streptomycin/100 ml of medium and 10% heat-inactivated feta calf serum, Sigma-Aldrich, USA). Cells were adjusted to $0.5 \times 10^6$ cells/well with differentiation medium (complete RPMI supplemented with 20 ng/ml M-CSF, R & D Systems Ltd, USA) and cultured in 24-well plates (Nunc) at 37° C., 5% $CO_2$. On day 3 of culture non-adherent cells were removed and the adherent cells were placed in fresh differentiation medium and the incubation was prolonged for 7 days to cause fully maturation of macrophages, which was assessed by fluorescence-activated cell sorting (FACS) analysis and 4/80 surface antigen expression.

bmMΦs were seeded into 24-well plates (Nunc) at $10^6$/ml in complete RPMI 1640 medium and then treated with a pre-determined concentration of Fh12 (5 μg/ml) for 30 min prior to being exposed to heat-killed *Listeria monocytogenes* (HKLM, $10^8$ cells/ml); Poly(I:C) (100 μg/ml); LPS (100 ng/ml); flagellin (1 μm/ml); imiquimod (10 μg/ml); or orthiazoloquinoline (CL075, 10 μg/ml). Control cells were treated with PBS, Fh12 or TLRs-ligands alone.

TLR Screening

Fh12-induced stimulation of TLRs was assayed in THP1-Blue™-CD14 cells expressing all TLRs as well as a reporter gene (secreted embryonic alkaline phosphatase; SEAP) driven by the NF-κB promoter (InvivoGen, San Diego, USA). Each TLR was induced with a known specific ligand as a positive control. Fh12 was assayed in concentrations between 1 to 20 μg/ml. Upon TLR stimulation; cells activate transcription factors and subsequently the secretion of SEAP, which is detected by using QUANTI-Blue™ medium that turns purple/blue in the presence of SEAP. Absorbance was read at 655 nm ($A_{655}$). Cells stimulated with PBS-endotoxin free were used as negative controls.

Phagocytosis Assay

The phagocytic ability of bmMΦs was measured using a CytoSelect™ 96-well phagocytosis assay (Cell Biolabs Inc.) that uses enzyme-labeled *Escherichia coli* particles as a phagocytosis pathogen. Briefly, bmMΦs were plated at $0.5 \times 10^6$ cell/ml and treated with Fh12 (5 μg/ml), LPS (100 ng/ml) alone or with Fh12 and LPS at the same time 2.5 h before addition of 10 μl/well of *E. coli* suspension. After 6 h of undisturbed incubation, the supernatants were gently aspirated and adherent cells were fixed with 3.2% buffered formaldehyde solution, and blocked for 30 min at room temperature (RT) in an orbital shaker. Cells were washed three times with PBS, and permeabilized by incubation with 100 μg/well of 1% Triton-X100 in PBS for 5 min. After another washing step the substrate solution was added and the mixture was incubated for 30 min at RT. The reaction was stopped and absorbance was read at 450 nm. Cells treated with 2 μM Cytochalasin-D were used as control for phagocytosis inhibition as per the manufacturer's instructions.

NF-κB Activation in TLR4-Transfected HEK Cells

To investigate the mechanism of interaction between Fh12 and TLR4 we used Human Embryonic Kidney 293 cells (HEK293, InvivoGen). These cells (HEK293-TLR4) are co-transfected with genes encoding cluster differentiation antigen-14 (CD14), myeloid differentiation protein-2 (MD2), toll-like receptor-4 (TLR4) co-receptor, and a SEAP reporter gene (HEK293-TLR4). Cells were maintained in DMEM supplemented with 4.5 g/L glucose, 10% fetal bovine serum (FBS), 50 U/ml penicillin, 50 μg/ml streptomycin, 100 μg/ml Normocin™ and 2 mM L-glutamine. For all experiments a cell suspension was prepared using HEK-Blue™ Detection medium at $14 \times 10^4$ cells/ml. For stimulation experiments, cells were seeded at $2.52 \times 10^4$ cells/well in 96-well flat-bottom plates and treated with Fh12 (from 0.62 to 10 μg/ml) or LPS (5 μg/ml), and incubated at 37° C., 5% $CO_2$ for 24 h. In the inhibition experiments, cells were cultured with Fh12 (0.6 to 10 μg/ml) 30 min prior LPS (5 μg/ml) stimulation. Cells cultured with polymyxin-B (PMB, 100 μM) (Invivogen) were used as an antagonist control. In other experiments, cells were stimulated with LPS (5 μg/ml) and then cultured with Fh12 (5 μg/ml) 30 min, 1, 2 and 4 after LPS-stimulation. All readings were done at 655 nm after 24 h of LPS-stimulation. Cells treated with PBS were used as a negative control. Cells treated with LPS were used as a positive control. The percent of reduction (R %) of the absorbance values was calculated by the formula R (%)=100−[(A−C)×100)/(B−C)], where A is the mean $A_{655}$ of three replicates obtained when cells were stimulated with Fh12, and B is the mean $A_{665}$ value obtained when cells were exposed to LPS, and C is the mean $A_{655}$ of three replicates obtained when cells were stimulated with PBS.

Cell Viability

To determine whether our experimental conditions affect cell viability HEK293-TLR4 cells or macrophages, cells were seeded at $2.52 \times 10^4$ cells/well in 96-well flat-bottom plates or at $0.5 \times 10^6$ cells/well and cultured in 24-well plates respectively. Cells were treated with LPS (100 ng/ml) and/or Fh12 (5 µg/ml) for 24 h or 48 h. Following incubation, cell viability was assessed by adding 50 µl XTT (sodium 3'-[1-(phenylaminocarbonyl)-3,4-tetrazolium]-bis(4-methoxy-6-nitro) benzene sulfonic acid hydrate) labeling reagent (Roche Life Science, USA) to each well. Following an additional incubation of 24 h at 37° C., the absorbance of each well was read at 480 nm.

Quantitative Real-Time PCR (qPCR) Analysis

Total RNA was extracted using a PureLink RNA Mini kit (Invitrogen) followed by treatment with Turbo DNAfree endonuclease (Ambion, Grand Island, N.Y.) to remove contaminating genomic DNA. RNA was quantified using a Nanodrop-1000 spectrophotometer (Thermo-Scientific, USA) and reverse-transcribed to cDNA by a High Capacity RNA-to-cDNA kit (Applied Biosystems, Carlsbad, Calif.). cDNA was amplified using a StepOne Plus Real-Time PCR system (Applied Biosystems) with cDNA equivalent to 5 ng of total RNA, and SYBR green PCR master Mix (Applied Biosystems). The cycling conditions were as follows: 95° C. for 15 min followed by 40 cycles of 95° C. for 15 s, 55° C. for 30 s, and 72° C. for 30 s. The primers used for each gene are listed in Table-1. Primer concentration was optimized and dissociation curves were generated for each primer set to verify the amplification of a single PCR product. qPCR experiments were conducted in triplicate using a StepOne Plus real-time PCR system (Applied Biosystems). The $2^{-\Delta\Delta Ct}$ method was used to quantify relative gene expression using β-actin as an internal control and expressed as fold change relative to expression in the control (cells stimulated with PBS). The values reported are the mean of three replicates. The standard deviation of the mean is shown as error bars in each group.

Protein Extraction and Western Blot

Total protein was extracted from cell lysates using radioimmunoprecipitation assay (RIPA) buffer containing 50 mM Tris-HCl, 150 mM NaCl, 1.0% NP-40, 0.5% sodium deoxycholate, 0.1% sodium dodecyl sulfate, and protease and phosphatase inhibitor cocktails (Sigma Aldrich). Cells were incubated in the extraction buffer on ice using a rocking platform for 30 min before being centrifuged at 20,000×g for 10 min at 4° C. Supernatants were transferred to clean tubes, and protein concentrations were determined using a BCA protein assay kit.

Protein samples (20 µg) and pre-stained protein markers (Precision Plus protein standards; Bio-Rad) were separated by 10% SDS-PAGE and blotted onto 0.45-µm nitrocellulose membrane (Bio-Rad). Membranes were blocked for 1 h at room temperature (RT) in 3% albumin in PBS and incubated overnight at 4° C. with the primary antibody. The antibodies used in this invention were: mouse monoclonal antibody to TLR4 (2 µg/ml), goat polyclonal antibody to CD14 (1 µg/ml), rabbit polyclonal antibody to MD2 (2 µg/ml) (Imgenex, San Diego, Calif., USA), mouse anti-β-actin (0.37 µg/ml) (Sigma) or rabbit anti-GPDH (1:10,000) (Abcam, Cambridge, Mass.). In the MAPK pathway studies we used: rabbit monoclonal antibodies anti-phospho-p44/42 MAPK (Erk1/2) (Thr202/Tyr204) and anti-p44/42 MAPK (Erk1/2) (Thr202/Tyr 204) diluted 1:2,000 (Cell Signaling Technology, Danvers, Mass.), rabbit anti-phospho-p38 MAPK (Thr180/Ty182), anti-p38 MAPK (D13E1), anti-phospho-SAPK/JNK (Thr183/Tyr 185), anti-SAPK/JANK (56G8) antibodies and rabbit anti-GAPDH antibody diluted 1:10,000. Membranes were washed in 50 mM Tris-HCl-buffered saline pH 7.5 (TBS) with 0.1% Tween-20 and incubated for 1 h at room temperature (RT) with the secondary antibody (anti-mouse IgG, anti-goat IgG or anti-rabbit IgG antibody) labeled with biotin. After additional washing steps, membranes were incubated 30 min at RT with a solution of avidin-peroxidase (Sigma-Aldrich) diluted 1:10,000 in PBS. Proteins were detected by addition of enhanced chemiluminescence substrate (Thermo Scientific). Densitometry analysis was performed on all immunoblots. Values were normalized to the PBS-treated control group and all values are expressed in arbitrary units as a percentage increase over the PBS control group.

LPS-Binding Protein (LBP)/LPS Interaction Assay

The Endoblock LBP ELISA test kit (Hycult Biotech, PA, USA) was used according to the manufacturer's instructions to investigate whether Fh12 disrupts the interaction between LPS and LBP. Briefly, binding of biotinylated LPS to pre-captured human LBP was assessed using streptavidin peroxidase, followed by addition of tetramethylbenzidine. Fh12 (0.05-10 µg/ml) was pre-incubated for 30 min with biotinylated-LPS and added to wells pre-coated with anti-LBP+LBP. PMB (0.2-100 µM), which competes with LBP for binding to LPS, was used as a control for inhibition by pre-incubation with biotinylated-LPS.

Immunofluorescence Staining

HEK293-TLR4 cells, and bmMΦs from naïve and CD14 knockout mice were grown for 48 h to 50% confluence on microscope coverslips and then treated for 4 h with LPS (1 µg/ml), Fh12 (5 µg/ml) or PBS. After the incubations, the cells were fixed for 10 min at 4° C. in cold acetone:methanol (1:1). After several washes with cold PBS, the cells were incubated for 30 min at RT with blocking solution (0.2% w/v gelatin, 0.5% w/v bovine serum albumin in cold PBS). After removing the blocking solution, the slides were placed in a humidity chamber and incubated overnight at 4° C. on a rocking platform with primary antibodies (rabbit anti-Fh12 IgG (1:50), mouse anti-lipid-A (1:10) (Abcam ab8467) or goat anti-CD14 (15 µg) (Imgenex IMG 3991) diluted in blocking solution. The cells were then washed six times 5 min each with cold blocking solution and incubated for 1 h with the corresponding secondary antibody (anti-rabbit IgG, anti-goat IgG or anti-mouse IgG) labeled with fluorescein isothiocyanate (FITC) diluted 1:2,000 in blocking solution. Nuclear chromatin was stained by incubation for 5 min in 0.5 mg/ml 4,6-diamidino-2-phenylindole (DAPI) (Bio-Rad). Preparations were mounted using ProLong Gold antifade reagent (Invitrogen, Carlsbad, Calif.). Images were observed with a Zeiss Observer Z1 confocal laser-scanning microscope coupled to a Zeiss LSM 510 Meta EC. The system was controlled using Zeiss ZEN 2009 software.

Immunostaining by In Situ Proximity Ligation Assay (PLA)

PLA was performed in HEK293-TLR4 cells to determine whether Fh12 could be interacting with CD14 co-receptor. Cells were grown to 50% confluence on BD BioCoat™ poly-D-lysine 8-well culture slides (BD Biosciences, Franklin Lakes, N.J.), and after 4 h of treatment with Fh12, LPS or PBS, were fixed as described above. After three washes with cold PBS, the cells were incubated with blocking buffer for 30 min. After removing the blocking solution, slides were placed in a humidity chamber and incubated overnight at 4° C. on an orbital platform with the pair of primary antibodies rabbit anti-Fh12 IgG and mouse anti-lipid A IgG or anti-Fh12 IgG and goat anti-CD14 IgG at the concentrations described above. Protein-protein interactions were detected using a Duolink II proximity ligation assay orange kit composed of anti-rabbit PLA probe minus, anti-mouse PLA probe minus and anti-goat probe plus (OLINK Biosience, Uppsala, Sweden) following the manufacturer's instructions. Images were observed with a Zeiss Observer Z1 confocal laser-scanning microscope coupled to a Zeiss LSM 510 Meta EC. The system was controlled using Zeiss ZEN 2009 software.

Docking Studies

The protein sequence of *F. hepatica* FABP1 (Fh15, Q7M4G0.3) was obtained from the UniProt database. No structures of these parasite proteins are known, thus models were prepared using the Protein Homology/AnalogY Recognition Engine (PHYRE) server, which predicts protein structure based on homology modeling. Human CD14 co-receptor structure (4GLP) was obtained from the PBD database. Proteins were docked using the ClusPro server. The top 10 balanced models were manually examined using PyMol (The PyMOL Molecular Graphics System, Version 1.5.0.4 Schrödinger, LLC.) and the distances between the LPS binding site and FABP1 residues examined and evaluated for relevance.

Statistical Analysis

All data were analyzed for normality prior to statistical testing. When comparisons of the values for multiple groups were made, data were analyzed using one-way analysis of variance. For comparison of values for two groups, the Student's t-test was used using Graphpad Prism software (Prism-6). For all tests, a P value of <0.05 was deemed significant.

Results

Purification of Native 12 kDa *F. hepatica* FABP (Fh12)

Purification of native *F. hepatica* FABP was previously optimized and published in detail. After the purification process, fractions containing a polypeptide band of around 12 kDa with isoelectric points of 5.1 to 7.25 were confirmed as FABP1 by mass spectrometry and its purity verified by 12.5% SDS-PAGE as recently reported. Fh12 gave endotoxin levels lower than 0.1 EU/ml, which is similar to background levels and to complete RPMI medium, so the purified Fh12 protein was considered to be endotoxin free.

Fh12 Suppresses Pro-Inflammatory Cytokines In Vivo in a Model of Septic Shock

Since it has been reported that helminthic infections, including inoculation with *F. hepatica* and other parasite antigens, prevent the symptoms of inflammatory diseases, we assessed whether Fh12 could suppress pro-inflammatory and inflammatory cytokines in vivo using a mouse model of septic shock.

C57BL/6 mice, 6 to 8 weeks old, were used. Groups of 5 animals each were injected intraperitoneally (i.p.) with a volume of 15 µl Fh12 (15 µg for each mouse), 1 h before i.p. injection with LPS (*E. coli* 0111:B4, 1 µg per each mouse). Control mice received PBS, Fh12 or LPS only (i.p.). Mice were sacrificed by cervical dislocation 12 h after LPS-exposure, and blood samples were taken by cardiac puncture. Concentrations of serum IFNγ, IL12p70, TNFα, GM-CSF, IL3, IL9, IL10, and IL15 cytokines were measured by cytokine microarrays.

As expected, intraperitoneal injection of 1 µg of LPS alone induced significantly higher levels of serum IFNγ (P<0.0001), IL12p70 (P<0.0002), IL3 (P<0.0005), IL9 (P<0.045), IL10 (P<0.0001), IL15 (P<0.0001), and TNFα (P<0.0021) compared to injection of PBS. Injections of Fh12 (15 µg) alone induced cytokine responses similar to those induced by PBS (data not shown). However, injection of mice with 15 µg Fh12 30 min prior to LPS-injection resulted in significantly reduced levels of IFNγ (P<0.0001), GM-CSF (P<0.006), IL12p70 (P<0.0002), IL3 (P<0.0003), IL9 (P<0.0029), IL10 (P<0.0001), IL15 (P<0.0001), and TNFα (P<0.0006) cytokines compared to LPS alone as appreciated in FIG. 1.

Fh12 Modulates the Production of Inflammatory Markers from Bone Marrow Derived Macrophages (bmMΦs) in Response to LPS.

Macrophages are very specialized antigen presenting cells and, when stimulated in vitro, they are excellent producers of pro-inflammatory cytokines. We previously demonstrated that Fh12 exerts a strong immunomodulatory effect on human macrophage-derived monocytes.

Figure 2:
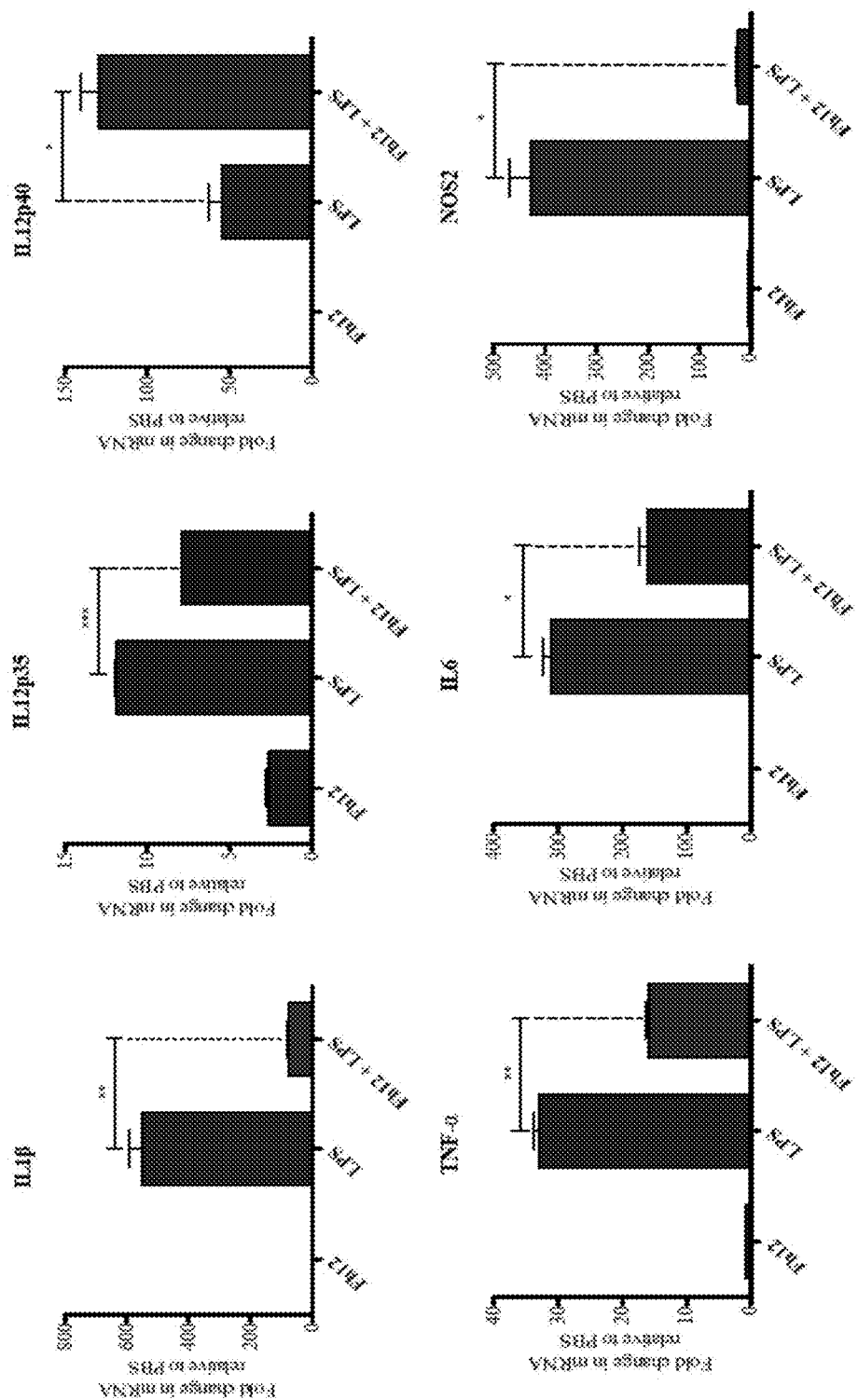
FIG. 2 shows plots of fold change in IL1β, IL12p35, IL12p40, TNFα, IL6 and NOS2 expression relative to cells stimulated with PBS, according to the present invention.

Macrophages from naïve C57BL/6 mice were treated with Fh12 (5 µg/ml) or PBS 30 min prior to stimulation with LPS (100 ng/ml) for 24 h. Control cells were treated with Fh12 or PBS alone. Expression of IL1β, IL12p35, IL12p40, TNFα, IL6 and NOS2 was measured in treated cells by quantitative RT-PCR (qPCR). Results are shown in FIG. 2 as the fold change in expression relative to cells stimulated with PBS and represent the mean±SD of a minimum of three experiments, each in triplicate. Values that were significantly different from the value for the group stimulated with LPS and Fh12+LPS are indicated as follows: *, P≤0.05, , P≤0.01, *, P≤0.001.

Our results here demonstrate that in the presence of Fh12 alone, bmMΦs do not express pro-inflammatory or inflammatory cytokines, which suggests that Fh12 does not activate any TLR on macrophages. However, treatment of bmMΦs with Fh12 prior LPS-stimulation resulted in a significant suppression of TNFα (P<0.0029), IL1β (P<0.0081), IL12p35 (P<0.0006) and IL-6 (P<0.0152) cytokines and NOS2 (P<0.0104) (FIG. 2). Concurrently to the suppression of Il12p35 we also found to be the subunit IL12p40 significantly over-expressed (P<0.0298) in cells treated with Fh12+LPS in comparison with cells that were treated with LPS only. An excess of the IL12p40 subunit may exert a profound inhibitory effect on IL12p70 functions, as has been reported in other studies; this is in agreement with the observed suppression of serum IL12p70 induced by Fh12 in the septic shock experiment.

Figure 3A:
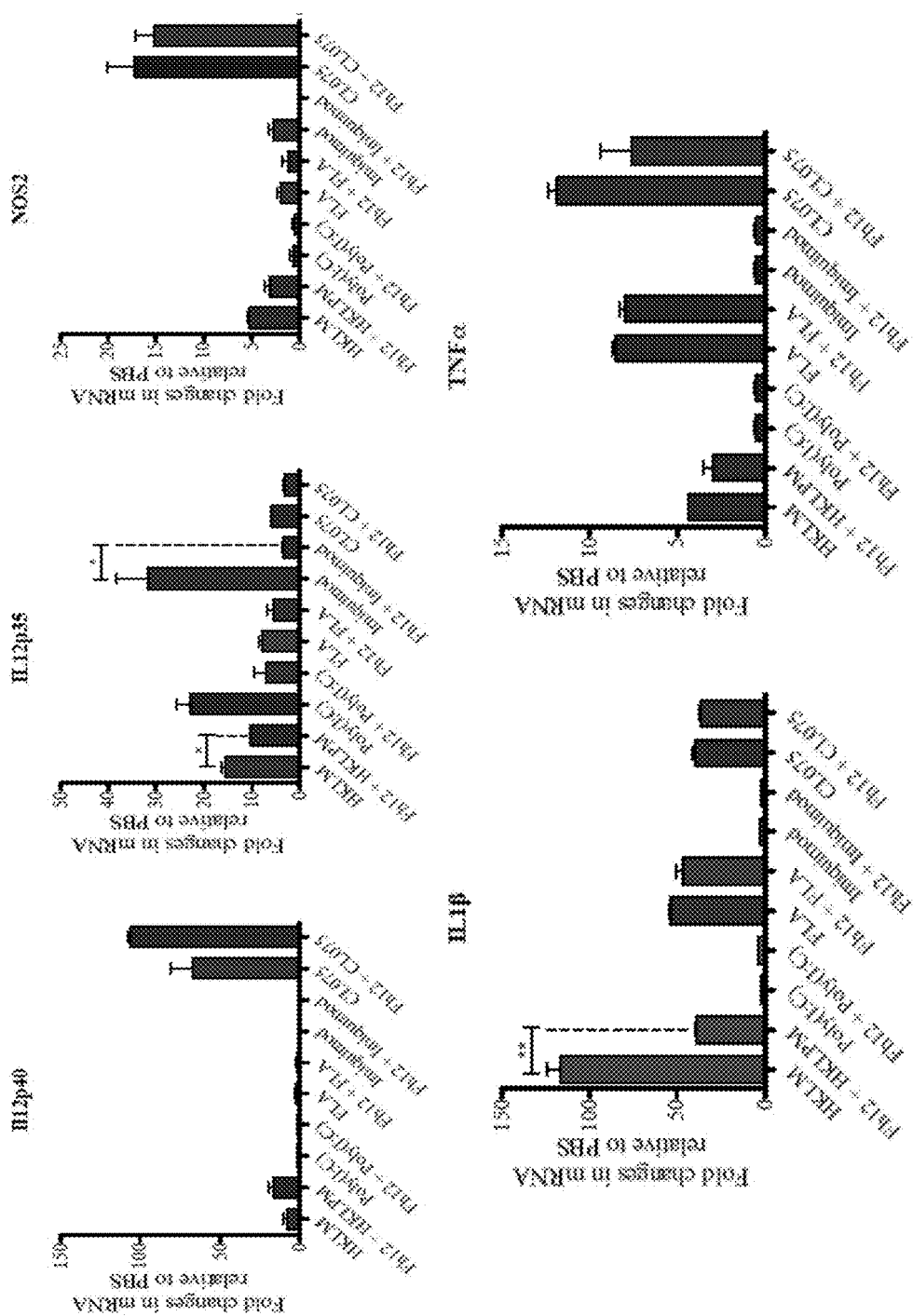
FIG. 3A shows additional plots of fold change in IL1β, IL12p35, IL12p40, TNFα, IL6 and NOS2 expression relative to cells stimulated with PBS, according to the present invention.

To determine whether Fh12 has a broad suppressive effect on macrophages rather than targeting a single TLR pathway, bmMΦs were cultured with Fh12 1 h prior to TLR-ligand stimulation with HKLM ($10^8$ cells/ml); Poly (I:C) (100 µg/ml); flagellin (1 µg/ml); imiquimod (10 µg/ml); and orthiazoloquinoline (CL075, 10 µg/ml). Fh12 had a limited effect on the cytokine expression profile of MΦs induced by ligands other than TLR4 since only suppressed the expression of IL1β (P<0.0084) and IL12p35 (P<0.089) in response to HKLM (TLR2-ligand), and the expression of IL12p35 (P<0.0499) in response to imiquimod (TLR7-ligand) but had not effect on other inflammatory markers induced by TLR2 or TLR7 nor on the expression of iNOS2 in response to other TLRs as shown in FIG. 3A.

Figure 3B:
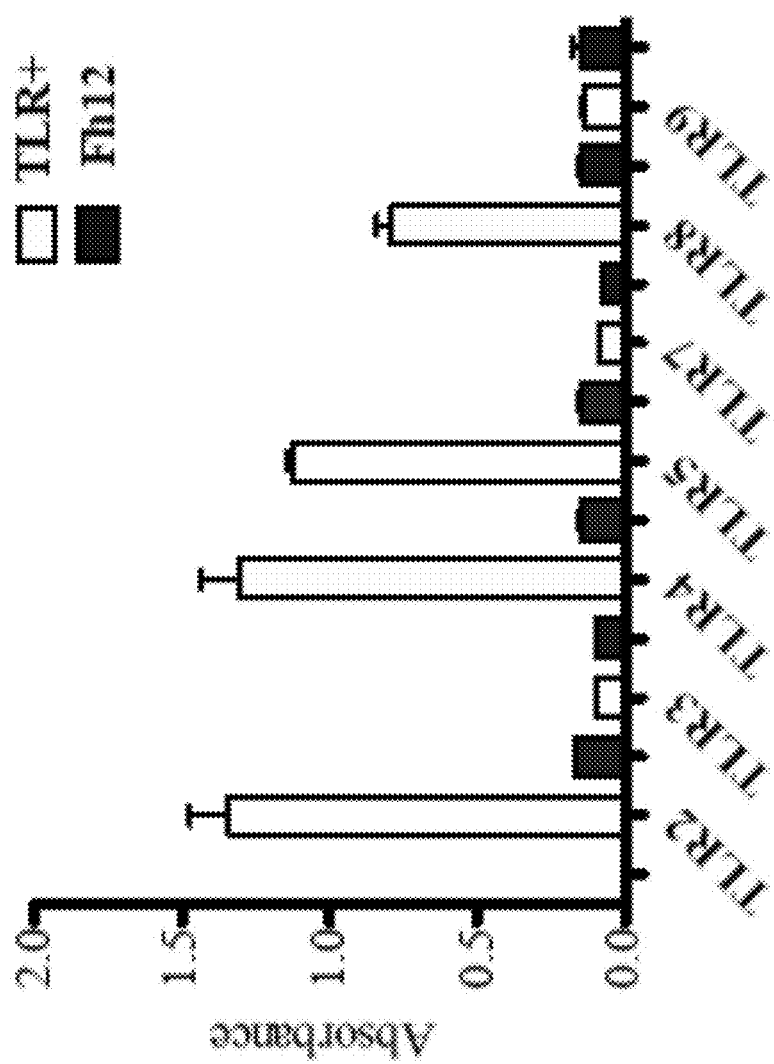
FIG. 3B shows a plot indicating the lack of involvement of TLR-activation in Fh12-mediated suppression, according to the present invention.

THP1-CD14-Blue cells, functionally expressing TLR-proteins as well as a reported gene, were stimulated with a specific agonist (TLR+) or Fh12 (5 µg/ml). Values that were significantly different from the value for the group stimulated with each TLR-ligand (TLR+) and Fh12 are indicated as follows: *, P≤0.05, , P≤0.01, *, P≤0.001. The lack of involvement of TLR-activation in Fh12-mediated suppression was further demonstrated by the absence of stimulation of THP1-CD14 or HEK293 cells which functionally express TLR proteins as shown in FIG. 3B.

Fh12 Suppresses Phagocytosis by Mouse bmMΦs

Phagocytosis is a major function of macrophages, allowing these key cells of the innate immune system to engulf and destroy foreign pathogens. To determine whether Fh12 was interfering with the phagocytic ability of bmMΦs, cells were cultured with PBS or LPS in the presence or absence of Fh12 prior to exposure to *E. coli* particles.

Bone marrow derived macrophages from naïve mice were cultured with PBS or LPS (100 ng/ml) in the presence and absence of Fh12 (5 µg/ml) prior to the addition of enzyme-labeled *E. coli* particles. Negative controls were treated with Fh12 alone or with 2 µM cytochalasin-D to block phagocytosis. Data are the mean (plus SD [error bars]) for three wells and are representative of three experiments. Values were found significantly different (P<0.001).

Figure 4A:
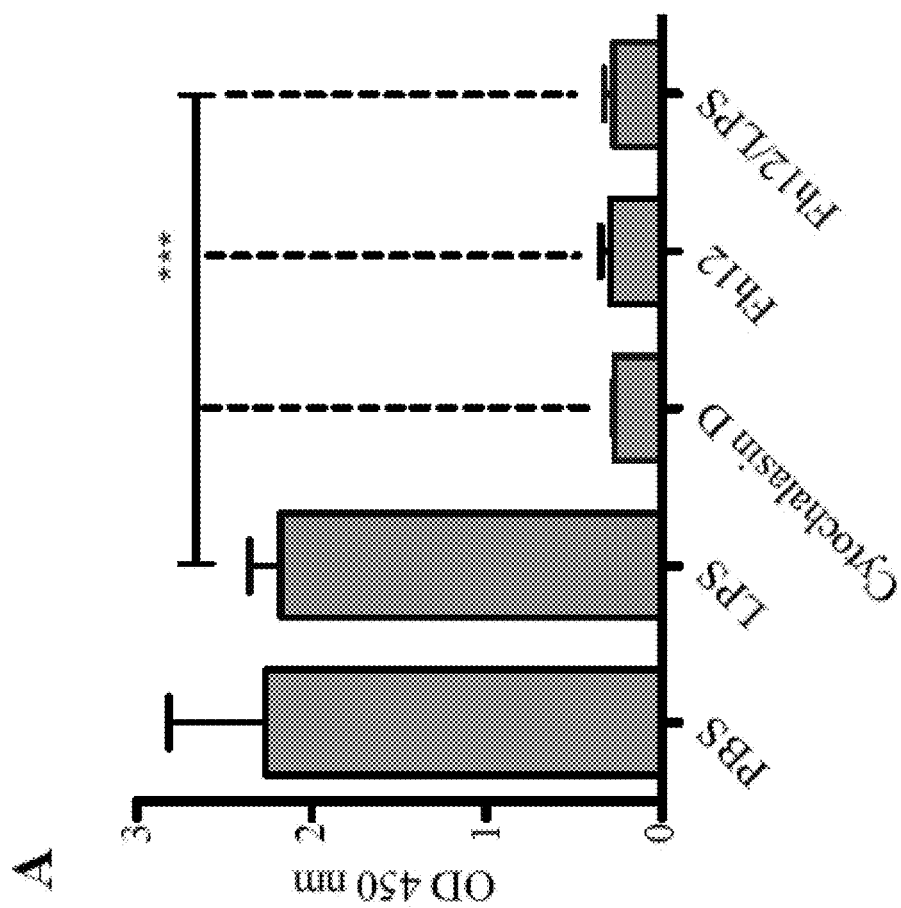
FIG. 4A shows a plot demonstrating that incubation with Fh12 alone did not induce phagocytosis of bacteria by macrophages and that incubation with Fh12 significantly suppressed the phagocytic ability of macrophages in response to LPS, according to the present invention.

The results demonstrated that incubation with Fh12 alone did not induce phagocytosis of bacteria by macrophages. Incubation with Fh12 significantly suppressed the phagocytic ability of macrophages in response to LPS (FIG. 4A; P<0.01). With such a potent inhibitory effect on macrophage function, we measured the influence of Fh12 on cell viability using an XTT assay.

Figure 4B:
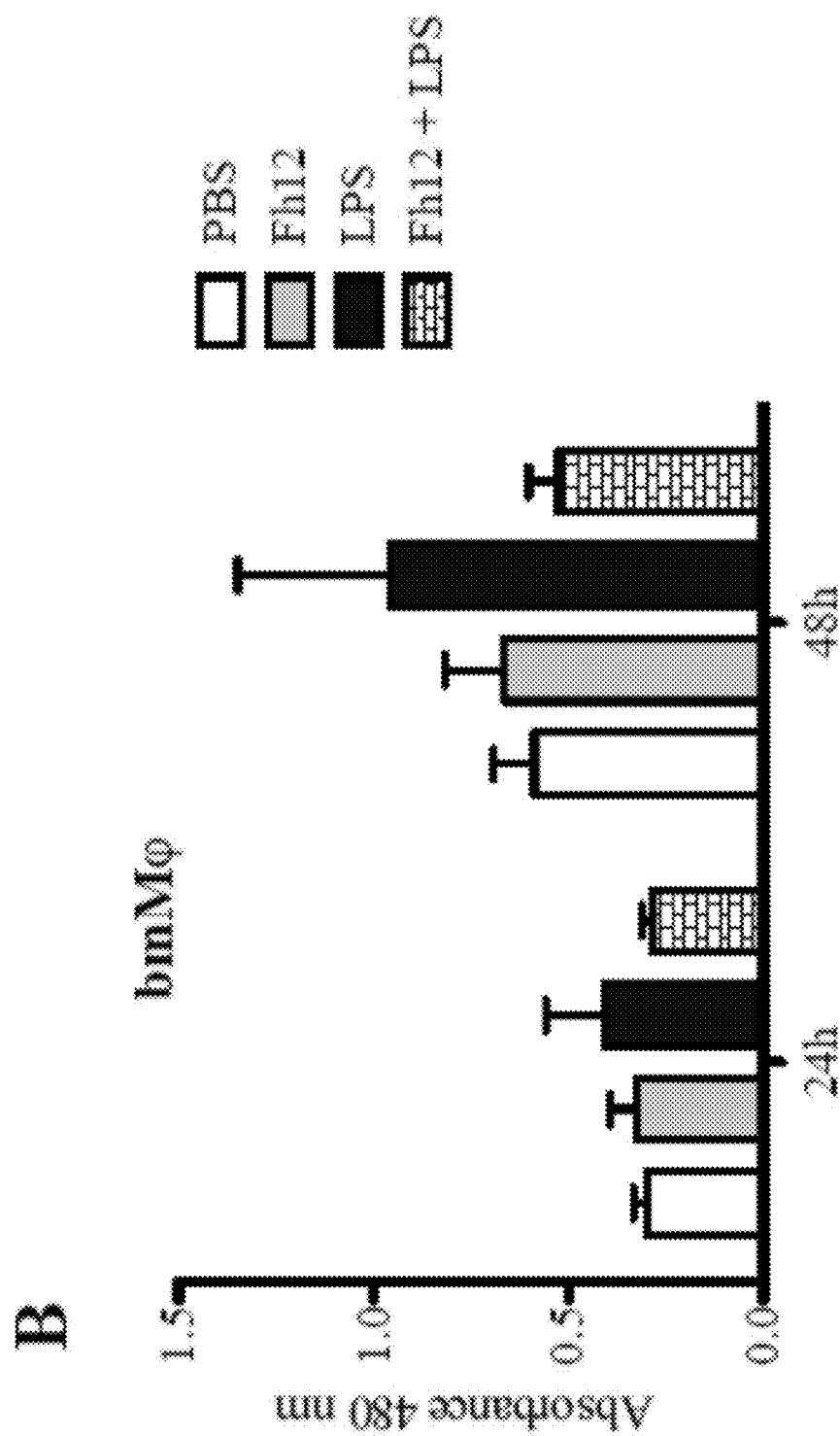
FIG. 4B shows a plot indicating treatment of macrophages with LPS, Fh12 or Fh12+LPS for 24 or 48 hours did not compromise the cell viability, according to the present invention.
Figure 4C:
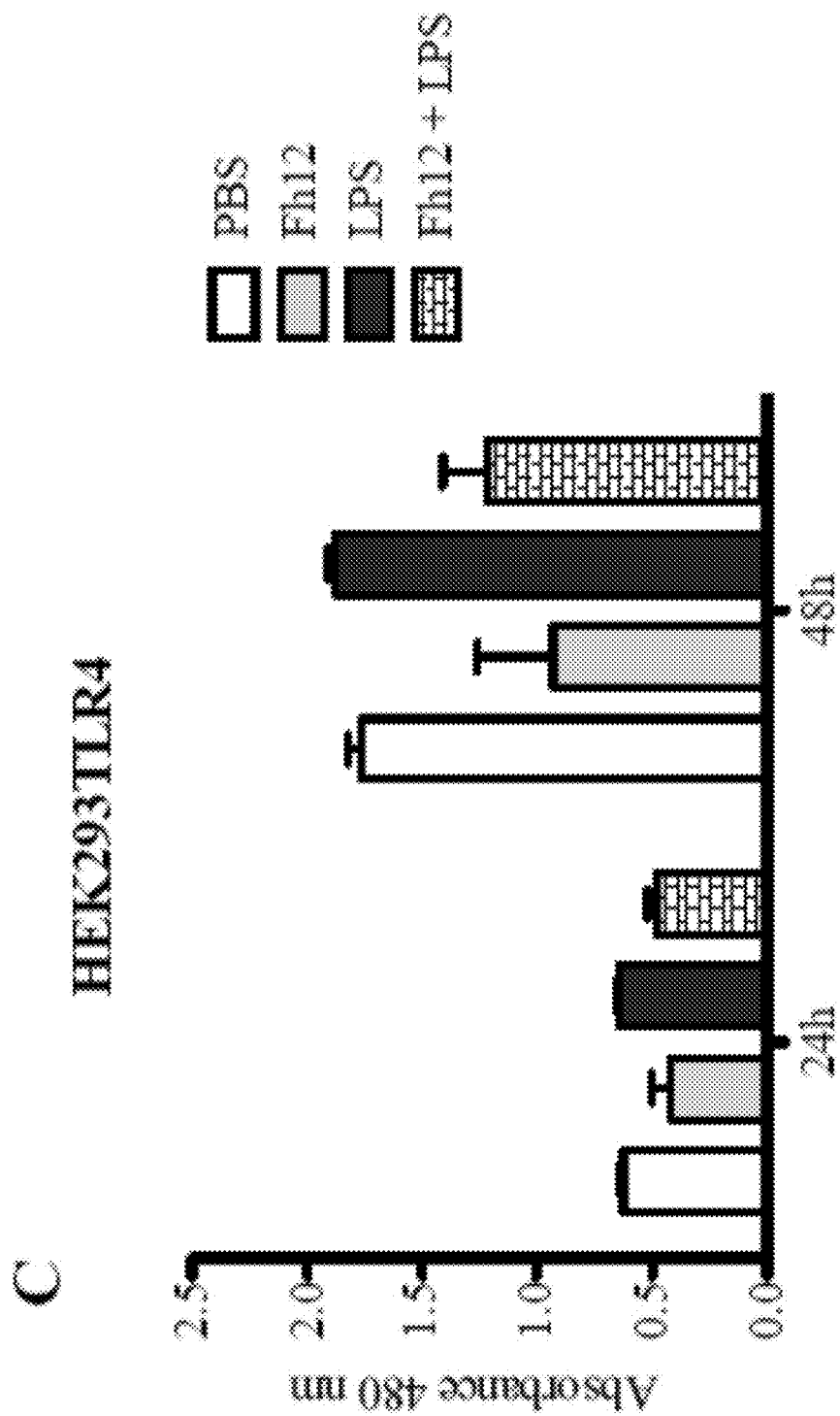
FIG. 4C shows a plot indicating treatment of HEK293-TLR4 cells with LPS, Fh12 or Fh12+LPS for 24 or 48 hours did not compromise the cell viability, according to the present invention.

Macrophages or HEK292-TLR4 cells from naïve mice were exposed to Fh12 (5 µg/ml), LPS (100 ng/ml) or Fh12 (5 µg/ml)+LPS (100 ng/ml) during 24 or 48 h. Cell viability was determined by adding 50 µl XTT to each well. Following an additional incubation of 24 h at 37° C., the absorbance of each well was read at 480 nm. The results demonstrated that treatment of HEK293-TLR4 cells or macrophages with LPS, Fh12 or Fh12+LPS for 24 or 48 hours did not compromise the cell viability as shown in FIGS. 4B and 4C. (FIG. 4B-C).

Fh12 Blocks LPS-Induced NF-κB Activation in HEK-293-TLR4 Cells

Based on the observed suppression of phagocytic activity and cytokine expression induced by LPS in the mouse model of septic shock, and the immunomodulation of helminth molecules via targeting TLR4, we focused on the interaction between Fh12 and TLR4 by using HEK293-TLR4 cells. By dose-response analyses, optimal concentrations of LPS and the antagonist polymyxin-B (PMB) were determined for subsequent analysis. A concentration of 5 µg/ml LPS induced maximum activation of the NF-κB transcription factor, and concentrations of 100 µM PMB completely suppressed NF-κB expression. When Fh12 was added to cells, NF-κB was not activated at any of the Fh12 concentrations used. To investigate whether the suppressive effect of is depending of the dose and the time of exposure cells were cultured with different concentrations of Fh12 30 min prior LPS-stimulation.

HEK293 cells co-transfected with genes encoding cluster differentiation antigen-14 (CD14), myeloid differentiation protein-2 (MD2), toll-like receptor-4 (TLR4) co-receptor, and a secreted embryonic alkaline phosphatase (SEAP) reporter gene (HEK293-TLR4), were maintained in DMEM and seeded at 2.52×104 cells/well in 96-well flat-bottom plates. The levels of NF-κB activation were estimated by readings at 655 nm, 24 h after LPS-stimulation. Cells were cultured with Fh12 (from 0.625 to 10 µg/ml) prior to stimulation with LPS. Cells cultured with PMB or PBS were used as the antagonist and negative controls, respectively. Cells stimulated with LPS were used as the activation control.

Figure 5A:
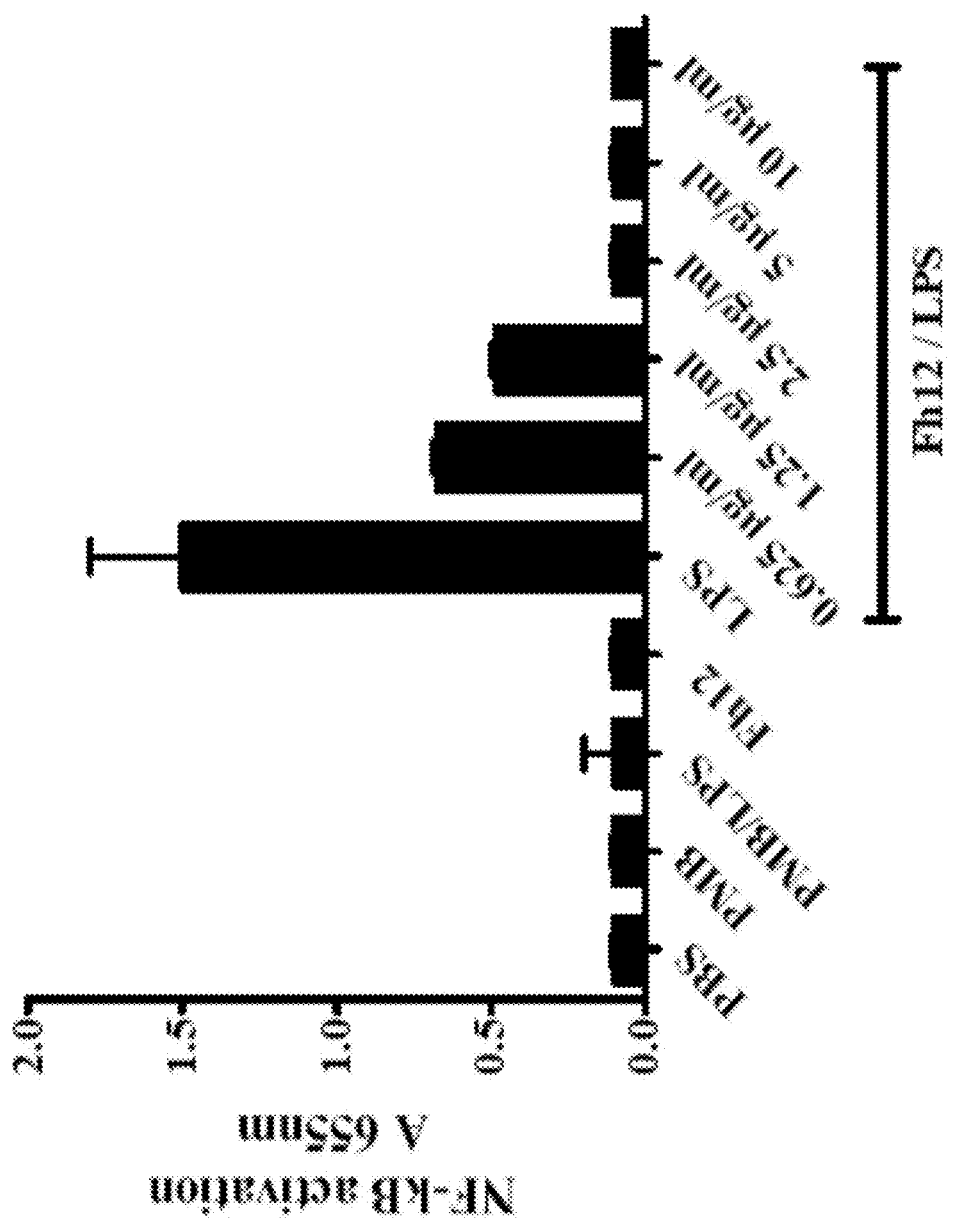
FIG. 5A shows a plot indicating the levels of NF-κB activation at 655 nm, according to the present invention.

The results demonstrated that, starting at 0.625 µg/ml, Fh12 suppressed NF-κB activation by 55%, and at concentrations ≥2.5 µg/ml, NF-κB activation was 100% suppressed, which is similar to the effect seen in the PMB control as shown in FIG. 5A.

Figure 5B:
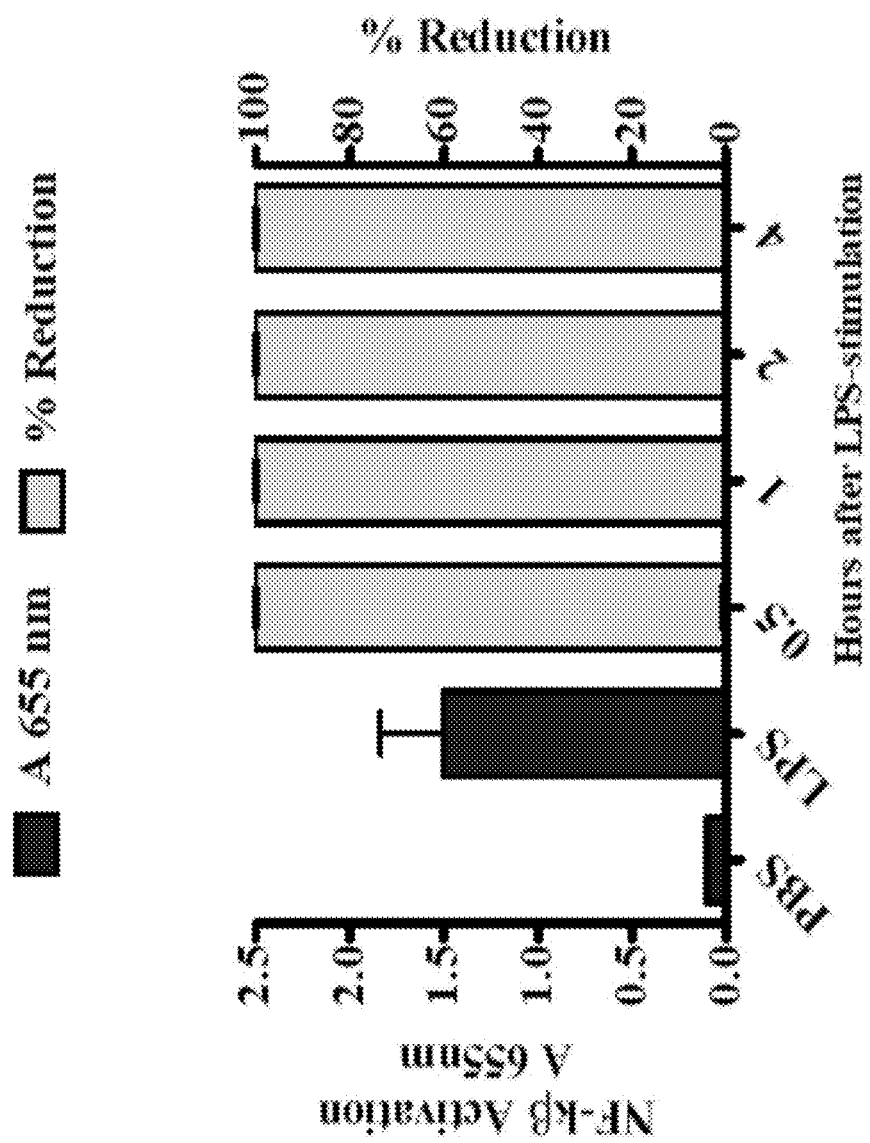
FIG. 5B shows a plot indicating that NF-κB activation is fully suppressed when Fh12 is added to cells between 30 min to 4 h after LPS-stimulation, according to the present invention.

To investigate whether Fh12 could suppress the activation of NF-κB after the cells have been stimulated with LPS, 5 µg/ml Fh12 was added at different time points (30 min, 1, 2 and 4 h) after LPS-exposure. Cells were stimulated with LPS (5 µg/ml) and then exposed to Fh12 (5 µg/ml) at different time points (30 min, 1, 2, 4 h) following LPS-stimulation. The reduction (R %) of NF-κB activation was calculated by the formula R (%)=100-[(A-C)×100/(B-C)], where A represents the mean NF-κB activation measured at 655 nm of three replicates obtained when cells were cultured with Fh12, B is the mean NF-κB activation measured at 655 nm when cells were stimulated with LPS, and C is the mean NF-κB activation measured at 655 nm when cells were stimulated with PBS. The results demonstrate that NF-κB activation is fully suppressed when Fh12 is added to cells between 30 min to 4 h after LPS-stimulation as shown in FIG. 5B.

Taken together, these results indicate that Fh12 block the entire TLR4 pathway in a manner that is dose-dependent and that the timing of exposure to Fh12 makes no difference.

Fh12 Suppresses the Phosphorylation of ERK, p38 and JNK in Response to LPS

Figure 11A:
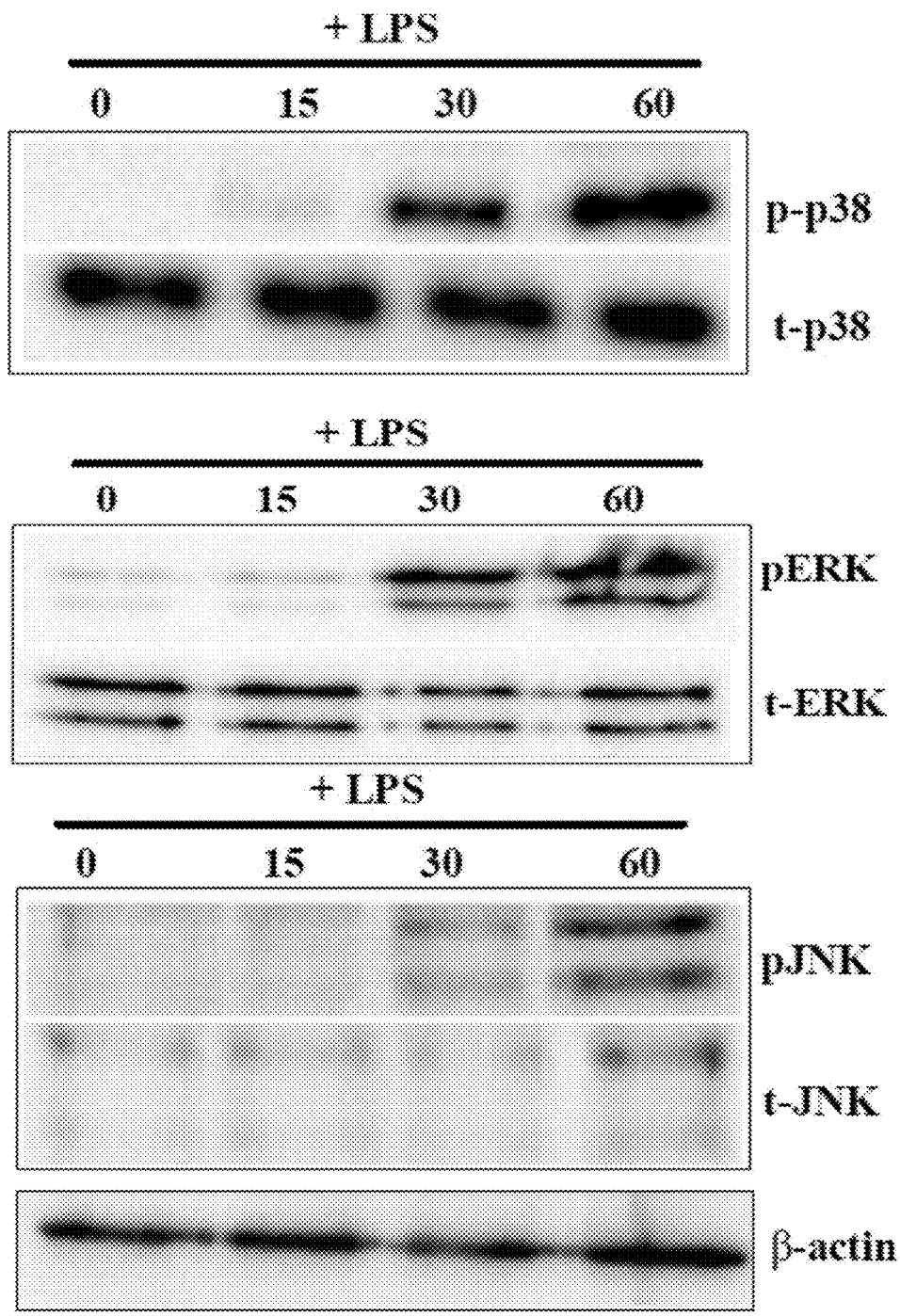
FIG. 11A shows western blot images for phospho (p)-ERK, total (t)-ERK, p-p38, t-p38, p-JNK, t-JNK and B-actin expression, according to the present invention.
Figure 11B:
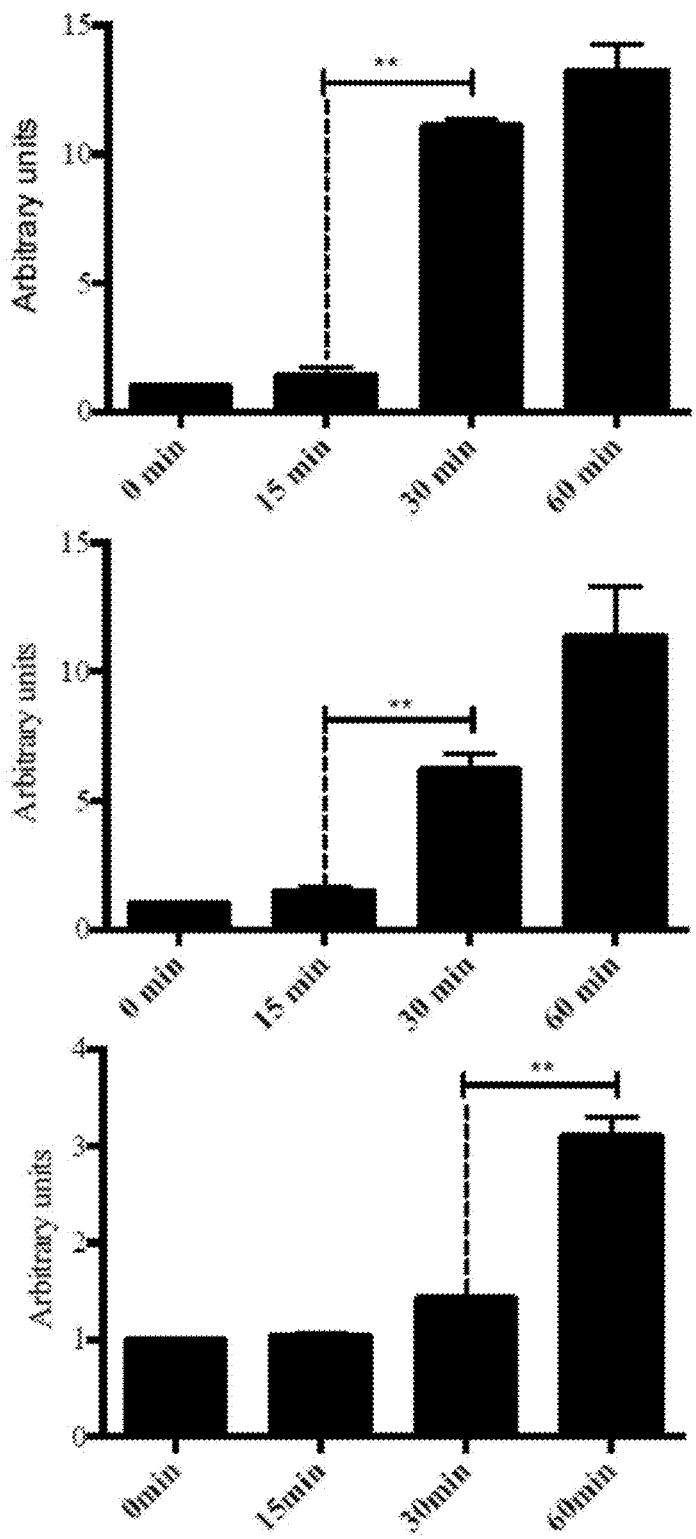
FIG. 11B shows plots indicating densitometry data presented as the mean+SD of the three independent experiments, according to the present invention.

Having demonstrated that Fh12 suppresses the expression of inflammatory cytokines of macrophages in response to LPS and suppress the NF-κB activation within HEK293-TLR4 cells incubated with Fh12 either before or after LPS-stimulation, we then investigated whether Fh12 might target common components of TLR pathways. Such targeting has been reported for mitogen-activated protein kinases (MAPKs) by other helminth products, such as *F. hepatica* tegumental antigens. To address this question, bmMΦs were cultured with Fh12 prior to or after LPS-stimulation and phosphorylation of ERK, JNK and p38 was measured. Initially, we measured the phosphorylation levels at different time points (15, 30 and 60 min) after LPS-stimulation and determined that the maximal phosphorylation levels of p38 and ERF are reached at 30 min, which is consistent with the findings of other authors in RAW267.7 cells, whereas the maximal levels of JNK phosphorylation are reached at 60 min as shown in FIGS. 11A-11B. In the Figures, bmMΦs were stimulated with 100 ng/ml LPS for 15, 30 and 60 min. Protein samples were analyzed by Western blot for phospho (p)-ERK, total (t)-ERK, p-p38, t-p38, p-JNK, t-JNK and B-actin expression. Densitometry data are presented as the mean+SD of the three independent experiments, wherein **P<0.005.

Figure 6A:
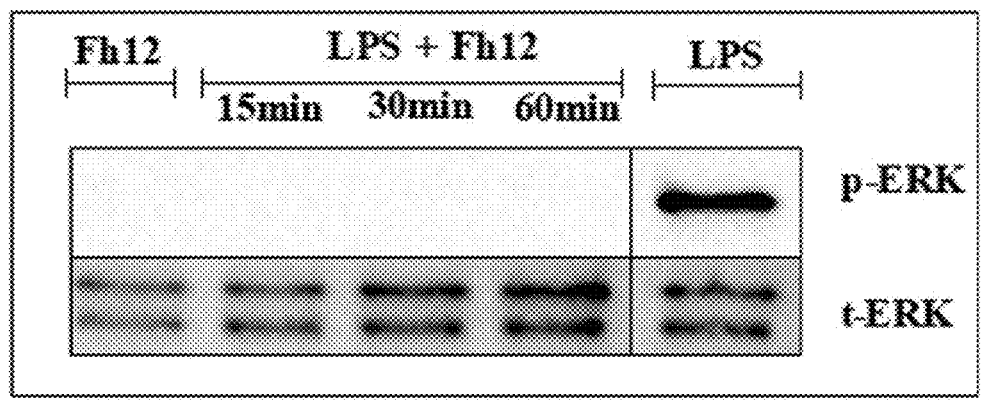
FIG. 6A shows western blot images for phosphorylated-ERK (p-ERK), total-ERK (t-ERK), phosphorylated-JNK (p-JNK), total-JNK (t-JNK), phosphorylated-p38 (p-38), total-p38 (t-p38) and β-actin expression, according to the present invention.
Figure 6A:
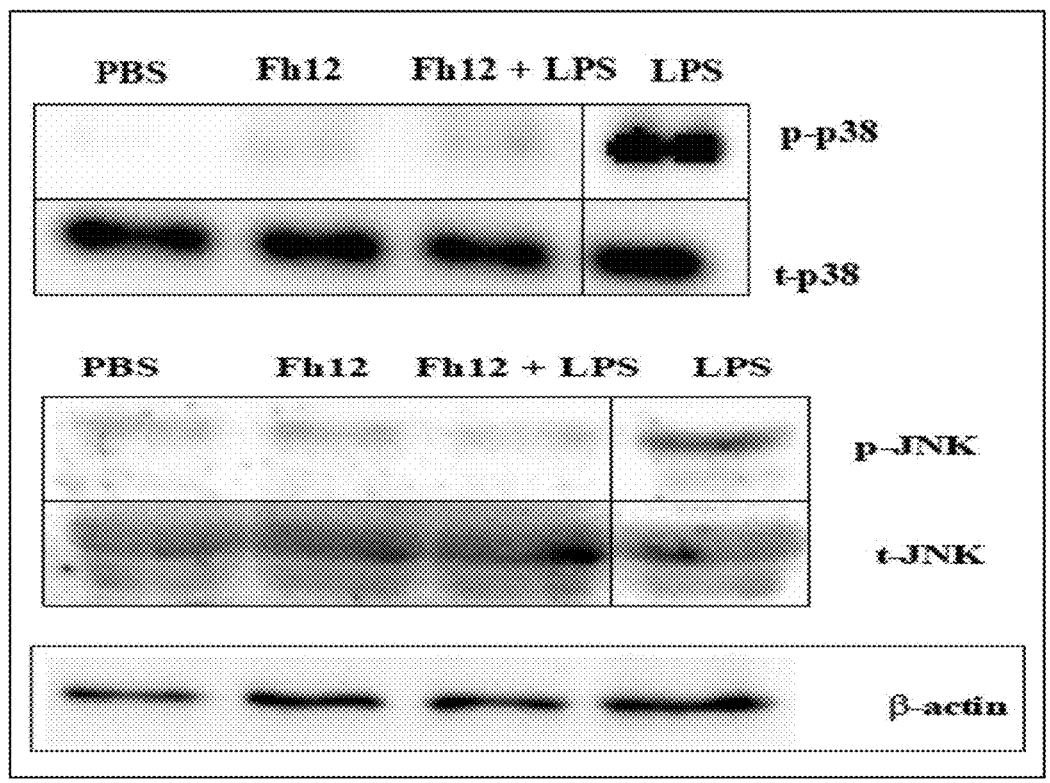
Figure 6B:
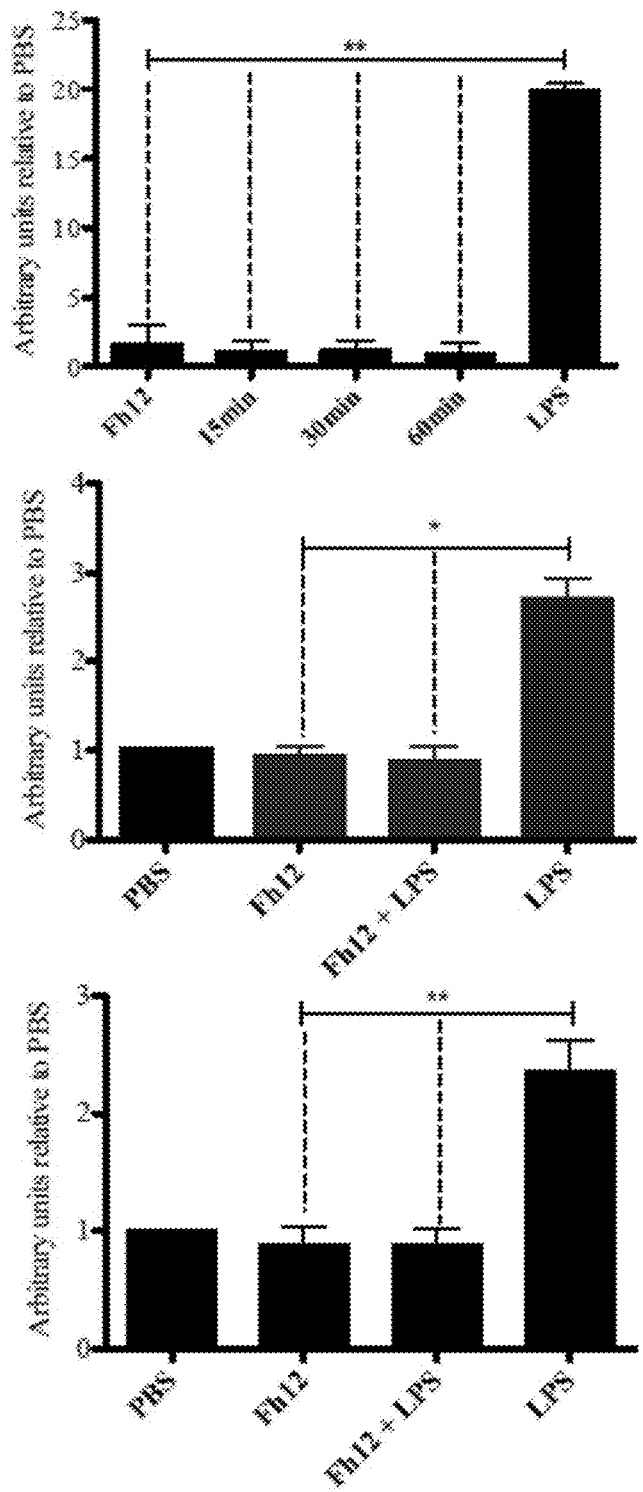
FIG. 6B shows plots indicating the values of p-ERK, p-JNK and p-p38 normalized to t-ERK, p-JNK or t-p38 and β-actin, respectively, and expressed in arbitrary units relative to the PBS control value, according to the present invention.

For the experiments shown in FIGS. 6A-6B, bmMΦs were stimulated with or without Fh12 (5 µg/ml) for 30 min prior to LPS stimulation (100 ng/ml) for 15, 30 min or 60 min (for ERK), 30 min (for p38) or 60 min (for JNK). Protein samples were analyzed by Western blot for phosphorylated-ERK (p-ERK), total-ERK (t-ERK), phosphorylated-JNK (p-JNK), total-JNK (t-JNK), phosphorylated-p38 (p-38), total-p38 (t-p38) and β-actin expression. Values of p-ERK, p-JNK and p-p38 were normalized to t-ERK, p-JNK or t-p38 and β-actin, respectively, and are expressed in arbitrary units relative to the PBS control value. These bands are representative of n=3, derived from the same gel for all treatments. The black lines on the figure indicate where parts of the image were joined. Densitometry data are presented as the mean±SD of three independent experiments, P≤0.05, P≤0.01, P≤0.001 compared with the control group. Fh12 alone did not induce phosphorylation of these components at any time point but was able to suppress significantly LPS-induced phosphorylation (p) of ERK (p-ERK, P<0.0035), p-JNK (P<0.001) and p-p38 (P<0.01) at every time point studied (FIGS. 6A-6B), which could explain the suppression of inflammatory markers induced by Fh12.

Fh12 Alters the Expression of Various TLR4 Pathway Components

Figure 7:
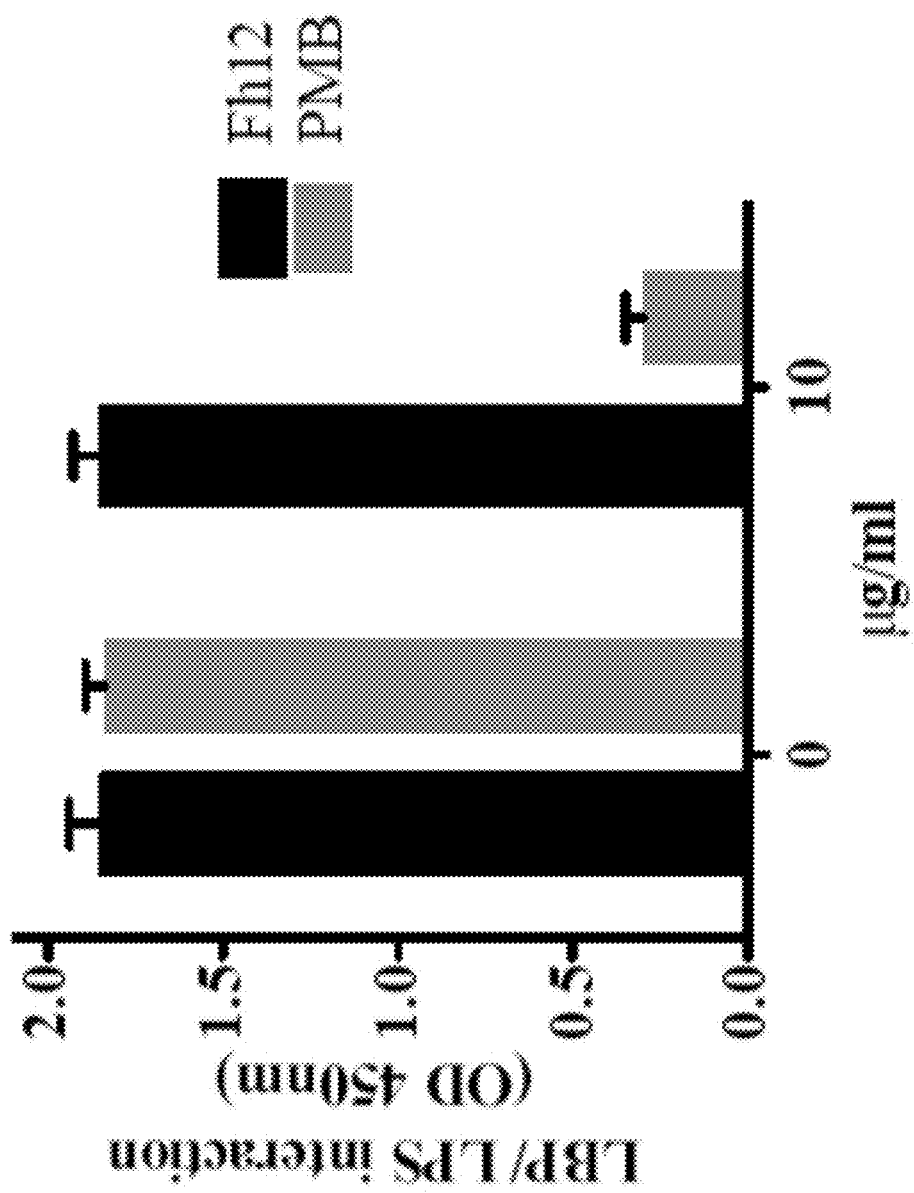
FIG. 7 shows a plot indicating that Fh12 did not prevent LPS binding to LBP after pre-incubation with either LPS or LBP, according to the present invention.

To investigate the mechanism through which Fh12 specifically blocks the interaction between LPS and TLR4, we firstly assessed whether Fh12 exposure alters either the interaction of LPS with lipid binding protein (LBP), or the expression of any TLR4 complex component. To assess whether Fh12 prevents binding of LPS to LBP, we used an LBP-ELISA kit, which detects binding of biotinylated LPS to LBP. PMB, which competes with LBP for binding to LPS, was used as a positive control. A lipid-binding protein assay (Endoblock) was used to investigate whether Fh12 disrupts the interaction between LPS and LBP. Polymyxin-B (100 µM), which is known to compete with LBP for binding to LPS, blocked LBP/LPS binding. Fh12 (10 µg) pre-incubated for 30 min with biotinylated-LPS and added to anti-LBP+ LBP was unable to block the (LBP/LPS) binding. At concentrations ≤10 µg/ml, Fh12 did not prevent LPS binding to LBP after pre-incubation with either LPS or LBP as shown in FIG. 7, indicating that Fh12 does not bind to LPS or LBP.

We next investigated whether Fh12 achieves its effect by regulating various components of the TLR4 complex and signaling cascades. The results show that Fh12 significantly reduced the expression of CD14 by more than 5-fold compared to cells stimulated with LPS alone, and this difference was found to be highly significant (P<0.001).

HEK293 cells were treated with 5 µg/ml Fh12 prior to stimulation with LPS (5 µg/ml). Cells stimulated with LPS were used as a positive control and cells treated with PBS were used as a negative control. After 24 h of incubation at 37° C., 5% CO2, the cells were lysed for RNA and protein extraction.

Figure 8A:
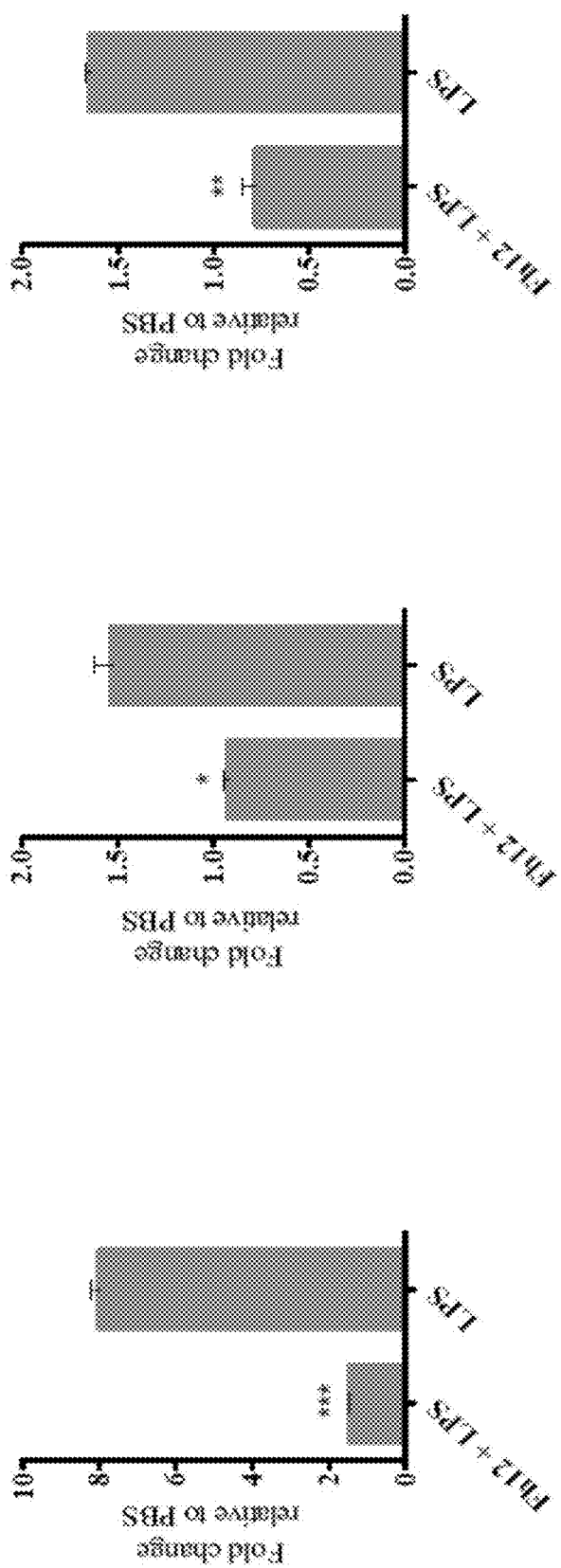
FIG. 8A shows plots indicating that Fh12 also reduced by 1.6-fold the expression of MD2 and by 2.1-fold the expression of TLR4 mRNA, according to the present invention.
Figure 8B:
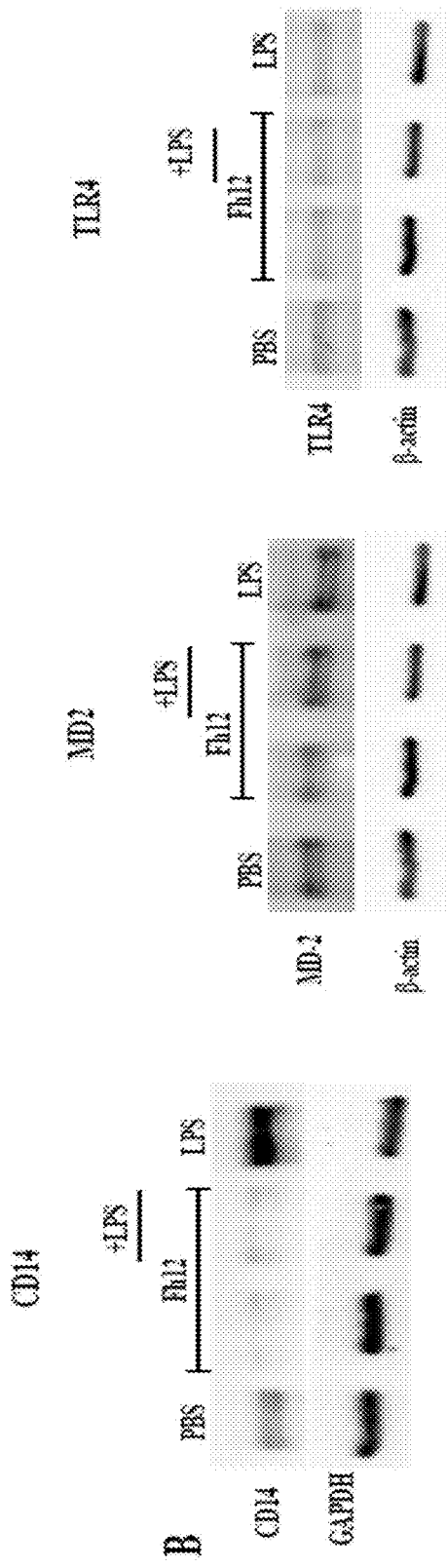
FIG. 8B shows western blot images of cells exposed to Fh12 prior to stimulation with LPS indicating the expression of CD14 protein was significantly reduced, according to the present invention.
Figure 8C:
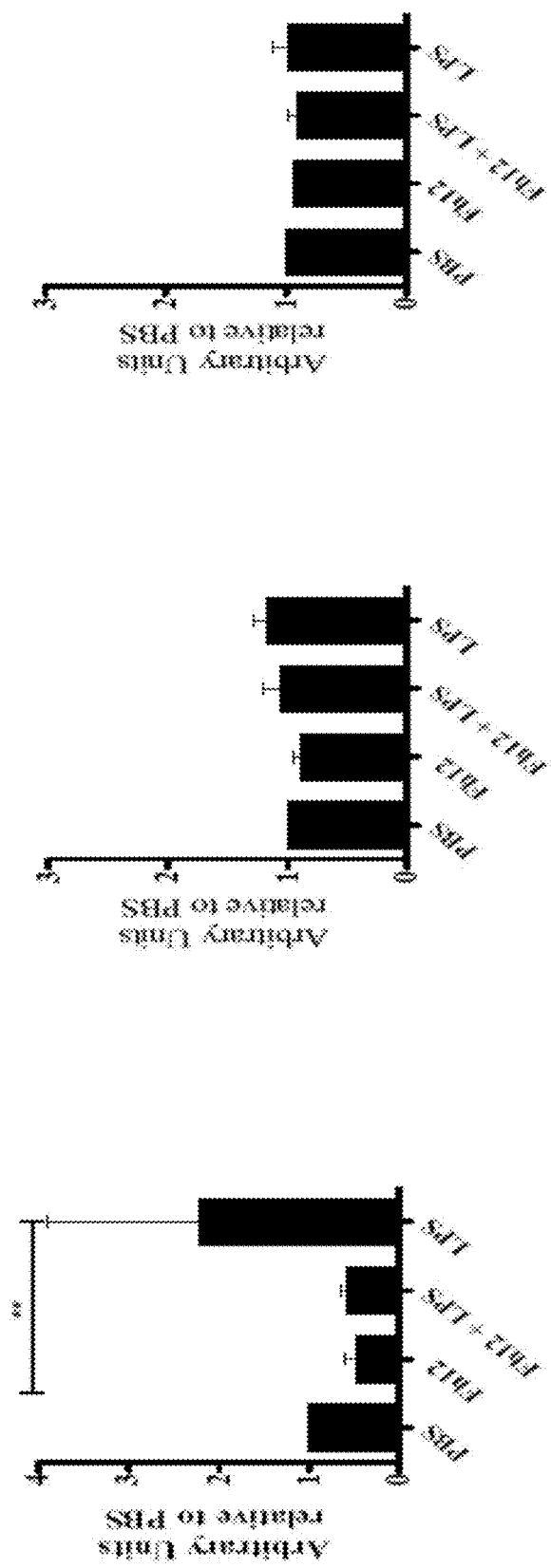
FIG. 8C shows plots indicating densitometric analysis performed on all immunoblots, according to the present invention.

Fh12 also reduced by 1.6-fold the expression of MD2 and by 2.1-fold the expression of TLR4 mRNA, and these reductions were both significant (P<0.05) as shown in FIG. 8A, where the expression of CD14, MD2 and TLR4 was determined by qPCR and results expressed as fold-changes relative to the PBS-control. Consistent with these results, the expression of CD14 protein was also significantly reduced (P<0.001), as detected by western blot analysis of cells exposed to Fh12 prior to stimulation with LPS (FIG. 8B). However, expression of MD2 and TLR4 protein was not significantly reduced following Fh12 treatment as shown in FIGS. 8B and 8C. In the Figures, protein extract (30 µg/sample of protein) was separated by 10% SDS-PAGE, transferred to nitrocellulose membrane and sequentially probed with anti-CD14, anti-MD2 or anti-TLR4 antibody. Immunoblots incubated with anti-GAPDH antibody was used as a control for protein concentration in the CD14 experiments. Immunoblots for MD2 and TLR4 were performed in the same experiment using anti-β actin antibody as a control for protein concentration. Representative blots are shown from three experiments. In FIG. 8C, densitometric analysis was performed on all immunoblots. Values were normalized to β-actin or GAPDH, and all values are expressed in arbitrary units as units of increase over the PBS control. P<0.005 compared with the PBS control group.

These results suggest that Fh12 might achieve its effect impacting the expression of CD14-coreceptor.

Fh12 Co-Localize on the Cell Surface and Interact with CD14-Coreceptor

To assess whether Fh12 could be in proximity to interact with the CD14-coreceptor, we employed the in situ proximity ligation assay (PLA), which was recently developed to detect and visualize protein-protein interactions. Results demonstrate that Fh12 localizes on the surface of cells in HEK293-TLR4 cells, which was also observed for LPS and CD14 co-receptor separately. Fh12 was also localized on the cell surface of bmMΦs generated from wild-type mice but not on the surface of macrophages from CD14 knockout mice, which confirms that Fh12 binds to the CD14-coreceptor as can be appreciated in FIGS. 12A-12F. In the Figures, HEK293-TLR4 cells were grown for 48 h to 50% confluence on microscope coverslips and then treated for 4 h with Fh12 (5 µg/ml), LPS (5 µg/ml) (positive control) or PBS (negative control). Cells were incubated respectively with anti-Fh12 antibody (diluted 1:50) (FIG. 12A), anti-lipid-A antibody (diluted 1:10) (FIG. 12B) or anti-CD14 antibody (15 µg) (FIG. 12C) followed by the correspondent anti-goat, anti-rabbit or anti-mouse secondary antibody labeled with FITC. Cells treated with PBS and incubated with anti-Lipid-A or anti-Fh12 were used as negative controls (FIG. 12D). Green fluorescence around cells demonstrates the specific localization of Fh12, LPS and CD14 on the cell surface. Fh12 was also localized on the surface of Fh12-treated naïve macrophages (FIG. 12E) but was not observed on the surface of macrophages from CD14 knockout mice (FIG. 12F).

Next, we performed the PLA using HEK293-TLR4 cells. HEK293 cells were grown for 48 h to 50% confluence on microscope coverslips and then treated for 4 h with LPS (5 µg/ml), Fh12 (5 µg/ml) (positive control), or PBS (negative control). As expected, by using the control pair of antibodies anti-Lipid-A and anti-CD14, a large number of intense orange dots were observed around cells as shown in FIG. 9A representing cells treated with LPS and incubated with the pair of antibodies mouse anti-lipid A IgG (diluted 1:10) and goat anti-CD14 IgG (15 µg). This indicates co-localization and interaction of LPS and CD14 co-receptor. Similarly, numerous intense orange dots were also observed when the experiment was performed with the pair of antibodies anti-Fh12 and anti-CD14 antibody, demonstrating closes proximity and interaction of Fh12 and CD14 as shown in FIG. 9B representing cells treated with Fh12 incubated with the pair of antibodies anti-Fh12 IgG (diluted 1:50)+goat anti-CD14 IgG (15 µg). No orange dots were observed in cells treated with PBS incubated with the anti-Fh12 and anti-CD14 antibodies simultaneously as shown in FIG. 9C representing control cells treated with PBS and incubated with the pair of antibodies anti-lipid A IgG (diluted 1:10) or anti-Fh12 IgG (diluted 1:50) and anti-CD14 IgG (15 µg), demonstrating there were no nonspecific interactions in this assay. The numerous orange dot signals around the cells show the typical interaction between LPS and CD14 co-receptor (FIG. 9A) and between Fh12 and CD14 (FIG. 9B). The images were observed with a Zeiss Observer Z1 confocal laser-scanning microscope coupled to a Zeiss LSM 510 Meta EC. The system was controlled using Zeiss ZEN 2009 software.

Figures 9D, 9E:
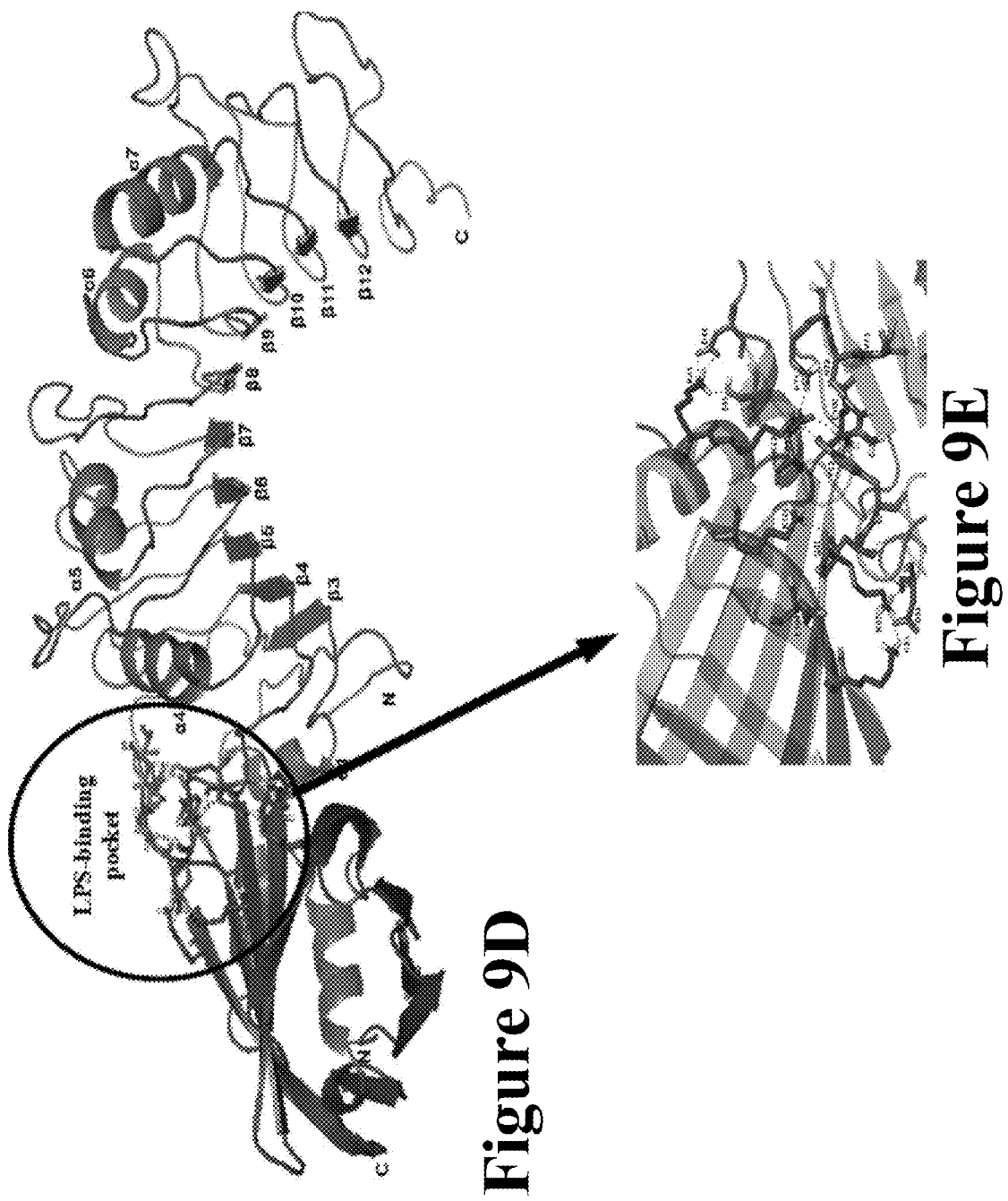
FIG. 9D shows a docking analysis between FABP1 and human CD14 co-receptor, according to the present invention.
FIG. 9E shows an amplified view of FIG. 9D illustrating interaction among residues, according to the present invention.

Furthermore, the modeled structure of human CD14 and the predicted tertiary structure of *F. hepatica* FABP were subjected to docking analysis to investigate potential molecular interactions between the two molecules. Docking analysis between FABP1 and human CD14 co-receptor was performed using the ClusPro server, demonstrating the potential interaction of FABP1 with the LPS-pocket localized on the structure of CD14. FIG. 9E is an amplified view showing interaction among residues K21, K22, K83, K97, E100, E104 and D122 of the model structure of FABP1 (purple color) are predicted to interact and bind with the residues D44, S46, K71, N72, V73, Y82, Q81 and D84 of the LPS binding pocket of the CD14-coreceptor (gray color) as shown in FIG. 9D and FIG. 9E.

Although Fh12 Binds to CD14 its Anti-Inflammatory Effect could be Independent of this Co-Receptor.

Having demonstrated that Fh12 binds and interacts with the CD14 co-receptor we proceeded to investigate whether CD14 is essential for the anti-inflammatory action of Fh12. We therefore exposed bmMΦs generated from CD14 knockout mice to LPS and HKLM in the presence of Fh12 and measured the expression of IL1β and IL12p35 cytokines, which were suppressed by Fh12 in the wild-type mice in response to TLR4 and TLR2-ligands.

Figure 10:
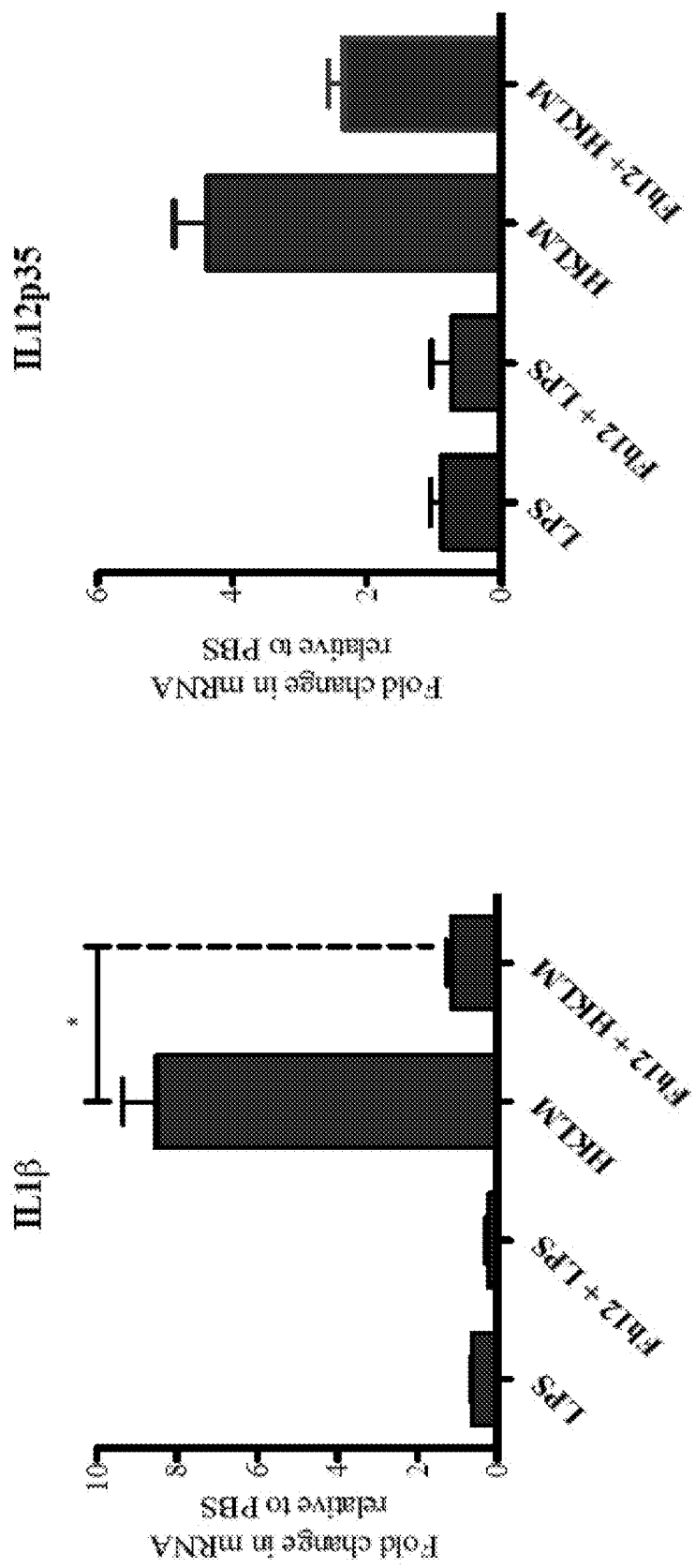
FIG. 10 shows plots indicating the expression of IL12p35 and IL1β as the fold changes relative to cells stimulated with PBS, according to the present invention.

Bone marrow derived macrophages were isolated from CD14 knockout mice and stimulated with LPS (100 ng/ml) or HKLM (108 cells/ml) in the presence or absence of Fh12 (15 µg/ml) for 24 h. Expression of IL12p35 and IL1β was determined by qPCR. The results shown in FIG. 10 are shown as the fold changes in expression relative to cells stimulated with PBS and represent the mean±SD of a minimum of three experiments, each in triplicate. Values that were significantly different from the value for the group stimulated with TLR-ligand and Fh12+TLR-ligand are indicated as *P≤0.05. The expression of IL1β and IL12p35 in response to LPS was found significant lowered in CD14 knockout compared to wild type (P<0.0001), which is an expected finding since it is well known that CD14 is an essential co-receptor for the activation of the TLR4-cascade. Similarly, the expression of both cytokines in response to HKLM was also found significantly reduced in knockout compared to wild type (P<0.0059). We found that Fh12 did not affect the expression of IL1β or IL12p35 of CD14 knockout mice in response to LPS and neither affects the expression of IL12p35 in response to HKLM. However, it suppressed the expression of IL1β in response to HKLM (P<0.013). These results suggest that CD14 co-receptor could not be the only target used by Fh12 to exert its anti-inflammatory effect.

Discussion

*F. hepatica* fatty acid binding proteins are immunogenic proteins of 12-15 kDa that play important roles in nutrient acquisition and survival of the parasite within the mammalian host. Although FABPs are considered cytosolic proteins, in proteomic studies two FABP isoforms (FABP1 and FABP2) have been identified among the ESPs of the liver fluke. Also, FABP1, known as Fh15, has been located in abundance at the surface of *F. hepatica*, indicating a possible role in the uptake of fatty acids from the environment. Since the tegument is shed every 2 to 3 h during the course of infection, FABP1 may be released into the surrounding medium as the tegument is sloughed. Recently, by using proteomics, our research group identified FABP1 in *F. hepatica* tegument extracts, specifically in one fraction highly reactive with sera from patients with chronic fascioliasis. These results corroborate that *F. hepatica* FABP1 is exposed to the immune system and that specific antibodies are elicited against this protein during the course of active infection. Thus, as for many other *F. hepatica* molecules, FABP could interact with antigen-presenting cells during the course of the innate immunity response. Recently, studies demonstrated that *F. hepatica* tegumental antigens (FhTeg) target innate immune cells, inhibiting their ability to drive Th1 immune responses. Based on the above, we purified native *F. hepatica* Fh12 and assessed its interaction with innate immune responses.

The ability of helminth antigens to inhibit activation of DCs and macrophages in response to stimulation with bacterial ligands suggests they could be ideal therapeutic candidates for the treatment of chronic inflammatory conditions as septicemia. Indeed, septicemia is not a common event during helminth infection, which supports the therapeutic potential of helminth antigens. Using specific helminth molecules to target innate immune cell signaling will circumvent the problem of global immune suppression associated with parasite infection and also with current immunetherapies. Given that Fh12 is an antigen previously identified in ESPs and FhTeg, we investigated whether it could prevent chronic inflammation in a mouse model of sepsis. Our results showed that injection of Fh12 (15 µg) into mice prior to administration of a sub-lethal dose of LPS reduced significantly the serum expression of IFNγ, TNFα, GM-CSF, IL12p70, IL-3 and IL-15, which are all cytokines associated with inflammatory responses. *F. hepatica* has been reported to suppress Th1 responses in concurrent bacterial infections, thus demonstrating its anti-inflammatory effect in vivo. These findings support the therapeutic potential of Fh12 as an anti-inflammatory agent. It was unexpected to find that Fh12 also reduced the levels of IL-10, a cytokine generally associated with anti-inflammatory and regulatory responses, which was elevated in mice injected with LPS. At least one study has demonstrated that Th1 cells can produce IL-10; thus, our results emphasize that IL-10 is a versatile cytokine that could play different roles during infection.

To ascertain whether Fh12 could target TLR pathways, we optimized a screening system based on NF-κB activation using THP1-Blue-CD14. Fh12 did not activate NF-κB, indicating that it is not a ligand for any of the TLRs expressed on these cells. Since Fh12 is present in FhTeg, these results are consistent with those of previous studies, which reported failure of FhTeg to activate HEK-293 cells expressing a range of TLR-proteins. Although Fh12 alone failed to induce NOS2 expression and cytokine production of macrophages from naïve mice, treatment of macrophages with Fh12 rendered the cells hypo-responsive to LPS with significant reductions in NOS2, TNFα, IL12p35, IL6 and IL1β expression. NOS2 is an enzyme that catalyzes the production of NO from L-arginine, and its expression is directly associated with the classical activation of macrophages, as is expression of IL12p70, TNFα and IL1β. These findings are consistent with recent data obtained by our research group using naïve human macrophages, which showed an alternative activation pattern in the presence of Fh12 that was characterized by low levels of NOS2 and NO, and high levels of Arg-1, arginase activity and chitinase activity.

It was interesting that in the presence of Fh12 macrophages over-expressed IL12p40 and suppressed the expression of IL12p35. The IL12p40 subunit binds with either the p35 or p19 subunit to form the functionally active IL-12p70 or IL-23 cytokine, respectively, which are required for development of Th1 responses and plays a central role in the autoimmune process. As a result of the IL12p40 overregulation, homodimers are formed (IL12p80) that competitively bind to the common receptor component IL12Rβ1, which prevents IL12-mediated shock in the murine model. This differential regulation of both IL12 subunits induced by Fh12 could partially explain the low IL12p70 levels observed in the present invention. It is therefore consistent with the significant down-regulation of phagocytic capacity of macrophages and evidence the suppressive impact of Fh12 on the maturation and function of these cells. Because *F. hepatica* needs to suppress inflammatory processes to survive in the host, reduction of IL12p70, which is a Th1-driving cytokine, could influence the suppression observed during bacterial co-infection.

Fh12 significantly suppresses NOS2 as well as a large number of inflammatory cytokines in response to LPS but fails to suppress most of these markers in response to other ligands. This suggests that the anti-inflammatory effect of Fh12 mainly occurs through a single receptor, TLR4. Interestingly, *F. hepatica* tegument antigen (FhTg), of which Fh12 is a component, suppressed significantly a large number of inflammatory cytokines from DCs in response to several TLR-ligands. This apparent contradiction could be explained by the complex composition of FhTg, which contain a myriad of molecules as has been demonstrated in proteomic analysis, each of which has its own mechanism of immunomodulation. Thus, it is likely that molecules other than Fh12, with broader suppressive effects, on multiple TLRs might overlap the effect of Fh12.

To explore the mechanism by which Fh12 reduces the inflammatory response via TLR4, we tested Fh12 in HEK293 cells stably transfected with CD14, MD2 and TLR4 genes and a SEAP reporter gene, a system that permits direct and efficient detection of NF-κB when it is activated by stimulation with TLR4 ligands. The results demonstrate that Fh12 completely inhibited the TLR4-activation induced by LPS whether it was added to the cell culture medium either before or after LPS-stimulation, which is consistent with the results previously obtained with macrophages. Moreover, the fact that Fh12 was able to suppress NF-κB activation when added to the culture prior to or 4 hours after LPS-stimulation reinforces the prophylactic and therapeutic potential of this molecule for the prevention of bacteria-induced sepsis, as Fh12 blocks LPS-induced activation of innate immune responses. FhTg and parasites such as *Toxoplasma gondii* and *Brugia malayi* also inhibited the activation of NF-κB.

LPS is the major lipid present in the outer membrane of gram-negative bacteria and the induction of pro-inflammatory responses through TLR4 is achieved by the sequential and coordinate action of four principal proteins: LPS-binding protein (LBP), CD14, MD2 and TLR4. This process is initiated when LBP disaggregates LPS from the bacterial membrane and catalytically transfers it to CD14, which in turn shuttles LPS to MD2/TLR4 to form the activated (TLR4-MD2-LPS)2 complex that has a pivotal role in initiating the inflammatory cascade. Our results demonstrate that Fh12 does not bind LBP or disrupt the LPB-LPS binding, and although Fh12 reduced the levels of expression of MD2 and TLR4 at the RNA level, these reductions did not significantly impact the expression of MD2 and TLR4 proteins. However, Fh12 caused a significant reduction in the expression of CD14 protein. This observation strongly suggests that CD14 co-receptor is likely the target that Fh12 uses to block the LPS-TLR4 interaction. Moreover, the proximity ligation assay demonstrated that Fh12 co-localizes in close proximity to the CD14 co-receptor, and the docking analysis support Fh12-binding to the LPS-pocket, which is located within the 65 N-terminal residues and clusters around the hydrophobic pocket of the horseshoe-shaped structure of CD14. This is further supported by the failing of Fh12 to localize on the surface of cells from CD14 knockout mice. Also in CD14 knockout mice Fh12 lost the capacity to suppress IL12p35 and IL1β of macrophages that are released in response to LPS or HKLM, which are ligands that use CD14 in their respective activation cascades. The finding that Fh12 did not suppress IL1β in response to HKLM in CD14 knockout mice suggest that Fh12 could impact molecules downstream the signaling cascade such as mitogen-activated protein kinases (MAPKs) that are common to several TLRs.

The MAPKs are a highly conserved family of serine/threonine protein kinases involved in variety fundamental cellular processes such as proliferation and macrophage maturation through known ligands. Activation of the main mammalian groups, JNK, ERK and p38, culminates in the release of cytokines from macrophages following downstream activation of a signaling cascade involving adaptor proteins such as MyD88. In the present invention, we demonstrated that Fh12 suppresses the LPS-induced phosphorylation of ERK, JNK and p38 in mouse macrophages. Our findings correlate with studies performed by others in which FhTeg reduced the ERK-phosphorylation induced by LPS on DCs. A study using *Schistosoma mansoni* egg antigens reported a reduction in LPS-stimulated phosphorylation of ERK in murine DCs. Also, it was demonstrated that phosphorylation of NF-κB and ERK is crucial in Th2 immune responses induced by *Trichuris trichiura*. The fact that Fh12 does not induce but suppresses cytokine production could suggest that Fh12 has a role in the suppression of Th1-responses. However, we have yet to determine whether Fh12 drives Th2 or T-regulatory immunity. This hypothesis and the biological importance of these findings will be investigated in further experiments in which the therapeutic and prophylactic potential of Fh12 will be evaluated in vivo, including its effect on the function of antigen-presenting cells.

The selective targeting of CD14 co-receptor could be a way to inhibit the entire TLR4 pathway. Because CD14 is potentially a target of a new generation of antisepsis agents, the finding that Fh12 targets the CD14 co-receptor could have pharmacological applications. A glycoconjugate preparation from *Treponema* spirochetes (Tm-Gp) was also reported to inhibit the interaction of LPS with CD14, acting as an antagonist of TLR4; however, this preparation is chemically heterogeneous and it was not possible to determine the component responsible for the interaction. In other studies, synthetic lipids have been used to inhibit LPS-induced TLR4 activation in HEK293 cells by targeting the CD14 co-receptor. Benefits of suppressed TLR4 activation have been documented in several experimental models of lethal shock, as have the benefits of using anti-CD14 and anti-TLR4 antibodies in humans. Also, synthetic LPS antagonists such as Eritoran and Tak-242 have been tested in experimental models of endotoxic shock. In this context, the present invention offers a significant promising alternative, a well-characterized helminth protein (Fh12) obtained by a relatively inexpensive methodology that has anti-inflammatory properties mostly via TLR4.

In summary, this is the first invention to report the anti-inflammatory properties of *F. hepatica* fatty acid binding protein (Fh12) and its modulatory effect on macrophage function. Several novel findings stand out from the results being reported in this communication: a) that Fh12 blocks induction of inflammatory mediators in vitro and in vivo and doing so completely inhibit activation of TLR4 by LPS in a dose-dependent manner; b) that this anti-inflammatory effect occurs through various concurrent mechanisms: (i) Fh12 targets CD14 co-receptor. Thus, *F. hepatica* antigens with Fh12 as a constituent could be saturating CD14 on circulating monocytes in infected subjects rendering them refractory to LPS-induced inflammatory activation, (ii) Fh12 inhibits the activation of transcription factor NF-κB as well as ERK, JNK and p38, which is a common molecule of multiple TLR-pathways, and (iii) Fh12 overexpresses the IL12p40 subunit, which may have a profound inhibitory effect on IL12p70 function and consequently on macrophage maturation and function. Thus, this invention represents a significant contribution to the development of drugs that block either activation through TLRs or their downstream signaling pathways, leading to inhibition of the storm of inflammatory molecules implicated in the pathology of many diseases.

We claim:

1. A method of reducing TLR4-mediated inflammation on a mammal comprising: administering to said mammal an amount of *Fasciola hepatica* fatty acid binding protein (Fh12) that specifically binds to a CD14 co-receptor of a TLR4 protein of antigen-presenting cells effectively reducing activation of TLR4 and the inflammatory response on said mammal.

2. The method of claim 1, wherein said TLR4 mediated inflammation is reduced by blocking interactions between TLR4 and bacterial Lipopolysaccharide (LPS).

3. The method of claim 1, wherein said TLR4 mediated inflammation is reduced by down-regulating the expression of at least one inflammatory cytokine.

4. The method of claim 1, wherein said TLR4 mediated inflammation is reduced by suppressing the phosphorylation of at least one kinase downstream TLR4-signaling cascade.

5. The method of claim 3, wherein said at least one inflammatory cytokine is selected from the group consisting of: IFNγ, TNFα, IL-1β, IL-6 and IL-12.

6. The method of claim 4, wherein said at least one kinase is selected from the group consisting of: ERK, p38 and JNK.

7. The method of claim 1, wherein the administration of said (Fh12) impairs the phagocytic capacity of bone marrow-derived macrophages (bmMΦs).

8. The method of claim 1, wherein the administration of said (Fh12) suppresses the expression of inducible nitric oxide synthase (iNOS2) in bone marrow-derived macrophages (bmMΦs).

9. The method of claim 1, wherein said (Fh12) is administered intraperitoneally.

10. The method of claim 1, wherein said (Fh12) is administered prior to said mammal being exposed to bacterial Lipopolysaccharide (LPS).

11. The method of claim 1, wherein said (Fh12) is administered after said mammal is exposed to bacterial Lipopolysaccharide (LPS).

* * * * *